US009695221B2

(12) United States Patent
Hampson et al.

(10) Patent No.: US 9,695,221 B2
(45) Date of Patent: Jul. 4, 2017

(54) **RECOMBINANT OUTER MEMBRANE PROTEINS FROM *BRACHYSPIRA HYODYSENTERIAE* AND USES THEREOF**

(71) Applicant: Boehringer Ingelheim Vetmedica GmbH, Ingelheim am Rhein (DE)

(72) Inventors: David John Hampson, Beforddale (AU); Nyree D. Phillips, Kalamunda (AU); Tom La, Willetton (AU)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 14/654,221

(22) PCT Filed: Dec. 18, 2013

(86) PCT No.: PCT/EP2013/077107

§ 371 (c)(1),
(2) Date: Jun. 19, 2015

(87) PCT Pub. No.: WO2014/096013

PCT Pub. Date: Jun. 26, 2014

(65) Prior Publication Data

US 2015/0353610 A1 Dec. 10, 2015

(30) Foreign Application Priority Data

Dec. 21, 2012 (EP) .................................... 12199050

(51) Int. Cl.

| | |
|---|---|
| ***C07H 21/02*** | (2006.01) |
| ***C07H 21/04*** | (2006.01) |
| ***A61K 39/00*** | (2006.01) |
| ***C07K 14/20*** | (2006.01) |
| ***G01N 33/569*** | (2006.01) |
| ***C12Q 1/68*** | (2006.01) |
| ***A61K 39/02*** | (2006.01) |

(52) U.S. Cl.

CPC .......... *C07K 14/20* (2013.01); *A61K 39/0225* (2013.01); *C12Q 1/689* (2013.01); *G01N 33/56911* (2013.01); *A61K 2039/552* (2013.01)

(58) Field of Classification Search

CPC ......... A61K 39/00; A61K 39/02; A61K 39/04
USPC ................. 424/9.1, 9.2, 184.1, 185.1, 243.1; 536/23.1, 23.7

See application file for complete search history.

(56) References Cited

U.S. PATENT DOCUMENTS

| | | | |
|---|---|---|---|
| 5,882,655 | A | 3/1999 | ter Huurne et al. |
| 6,682,745 | B1 | 1/2004 | Jacobs et al. |
| 7,531,176 | B2 | 5/2009 | Hampson et al. |
| 7,569,682 | B2 | 8/2009 | Adler et al. |
| 8,460,681 | B2 | 6/2013 | Hampson et al. |
| 8,895,021 | B2 | 11/2014 | Hampson et al. |
| 8,992,938 | B2 | 3/2015 | Bellgard et al. |
| 9,011,878 | B2 | 4/2015 | Hampson et al. |
| 2004/0186280 | A1 | 9/2004 | Hampson et al. |
| 2005/0163791 | A1 | 7/2005 | Adler et al. |
| 2006/0057151 | A1 | 3/2006 | Hampson et al. |
| 2006/0153875 | A1 | 7/2006 | Adler et al. |
| 2006/0204522 | A1 | 9/2006 | Kroll et al. |
| 2007/0026017 | A1 | 2/2007 | Hampson et al. |
| 2008/0063655 | A1 | 3/2008 | Adler et al. |
| 2009/0017048 | A1 | 1/2009 | Adler et al. |
| 2010/0055124 | A1 | 3/2010 | Hampson et al. |
| 2010/0297178 | A1 | 11/2010 | Hampson et al. |
| 2011/0020383 | A1 | 1/2011 | Bellgard et al. |
| 2011/0064756 | A1 | 3/2011 | Hampson et al. |
| 2011/0064761 | A1 | 3/2011 | Hampson et al. |
| 2011/0293661 | A1 | 12/2011 | Hampson et al. |
| 2013/0330370 | A1 | 12/2013 | Hampson et al. |

FOREIGN PATENT DOCUMENTS

| | | | |
|---|---|---|---|
| WO | 9104036 | A1 | 4/1991 |
| WO | 9820899 | A1 | 5/1998 |
| WO | 03095480 | A2 | 11/2003 |
| WO | 2004007726 | A2 | 1/2004 |
| WO | 2006119983 | A2 | 11/2006 |
| WO | 2008017636 | A2 | 2/2008 |
| WO | 2010054437 | A1 | 5/2010 |
| WO | 2014096013 | A1 | 6/2014 |

OTHER PUBLICATIONS

Bellgard, M.I., et al. PloS One, vol. 4, Issue 3, e4641, pp. 1-12, Mar. 2009.*

Achacha et al., "Development of an Experimental Model Allowing Discrimination Between Virulent and Avirulent Isolates of Serpulina (Treponema) hyodysenteriae". Canadian Journal of Veterinary Research, vol. 60, No. 1, Jan. 1996, pp. 45-49.

Bellgard et al., "Genome Sequence of the Pathogenic Intestinal Spirochete Brachyspira hyodysenteriae Reveals Adaptations to Its Lifestyle in the Porcein Large Intestine". PLOS One, vol. 4, Iss. 3, Mar. 2009, pp. e4641.1-e4641.12.

Database UniProt Accession No. C0QVS1, "SubName: Full=OmpA family protein". May 5, 2009, 1 page.

Database UniProt Accession No. C0R2B4, "SubName: Full=OmpA family protein". May 5, 2009, 1 page.

Database UniProt Accession No. C0R2B5, "SubName: Full=Outer membrane protein". May 5, 2009, 1 page.

(Continued)

*Primary Examiner* — Rodney P Swartz

(74) *Attorney, Agent, or Firm* — Paula K. Wittmayer; Wendy M. Gombert

(57) ABSTRACT

The present invention relates generally to the field of diarrheal diseases caused by intestinal spirochaetes. Specifically, the invention relates to the prevention and/or treatment of infections with *B. hyodysenteriae*. In one aspect, the invention relates to a novel recombinant polypeptide, wherein said polypeptide may preferably be combined with one or more further recombinant polypeptides. In a further aspect, an immunogenic composition containing said recombinant polypeptide(s) is provided for use in a method for treating or preventing clinical signs caused by *Brachyspira hyodysenteriae*.

21 Claims, No Drawings

(56) References Cited

OTHER PUBLICATIONS

Davis et al., "The Brachyspira hyodysenteriae ftnA Gene: DNA Vaccination and Real-Time PCR Quantification of Bacteria in a Mouse Model of Disease". Current Microbiology, vol. 50, 2005, pp. 285-291.

Greenspan et al. "Defining epitopes: It's not as easy as it seems". Nature Biotechnology, vol. 17, Oct. 1999, pp. 936-937.

Hampson et al., "Brachyspira research—special issue on colonic spirochaetes of medical and veterinary significance". Journal of Medical Microbiology, vol. 53, 2004, pp. 263-265.

Hampson et al., "Influences of diet and vaccination on colonisation of pigs by the intestinal spirochaete Brachyspira (Serpulina) pilosicoli". Veterinary Microbiology, vol. 72, 2000, pp. 75-84.

Hampson et al., "Spirochaetes as intestinal pathogens: Lessons from a Brachyspira genome". Gut Pathogens, vol. 1., No. 10, May 2009, 3 pages.

Hampson, David, "Detection and Strain Typing of Brachyspira Hyodysenteriae to Support Swine Dysentery Eradication and Control". Report Prepared for the Co-Operative Research Centre for an Internationally Competitive Pork Industry, Murdoch University, Western Australia, Jul. 2008, pp. 1-39.

Harel et al., "Characterization of Serpulina hyodysenteriae Isolates of Serotypes 8 and 9 from Quebec by Restriction Endonuclease Fingerprinting and Ribotyping". Canadian Journal of Veterinary Research, vol. 58, 1994, pp. 302-305.

Holden et al., "An evaluation of the immunogenicity and protective responses to Brachyspira hyodysenteriae recombinant SmpB vaccination". Veterinary Microbiology, vol. 128, 2008, pp. 354-363.

International Search Report and Written Opinion for PCT/EP2013/077107 mailed Apr. 28, 2014.

Jungoh et al., "Soluble Expression of OmpA from Haemophilus parasuis in *Escherichia coli* and Its Protective Effects in the Mouse Model of Infection". Journal of Microbiology and Biotechnology, vol. 22, No. 9, 2012, pp. 1307-1309.

La et al., "Evidence that the 36 kb plasmid of Brachyspira hyodysenteriae contributes to virulence". Veterinary Microbiology, vol. 153, 2011, pp. 150-155.

La et al., "Protection of pigs from swine dysentery by vaccination with recombinant BmpB, a 29.7 kDa outer-membrane lipoprotein of Brachyspira hyodysenteriae". Veterinary Microbiology, vol. 102, 2004, pp. 97-109.

Li et al., "Serotyping of Canadian Isolates of Treponema hyodysenteriae and Description of Two New Serotypes". Journal of Clinical Microbiology, vol. 29, No. 12, Dec. 1991, pp. 2794-2797.

Stanton et al., "Isolation, Oxygen Sensitivity, and Virulence of NADH Oxidase Mutants of the Anaerobic Spirochete Brachyspira (Serpulina) hyodysenteriae, Etiologic Agent of Swine Dysentery". Applied and Environmental Microbiology, vol. 65, No. 11, Nov. 1999, pp. 5028-5034.

Yan et al., "Identification and characterization of OmpA-like proteins as novel vaccine candidates for Leptospirosis". Vaccine, vol. 28, 2010, pp. 2277-2283.

* cited by examiner

SEQUENCE LISTING

```
<160> NUMBER OF SEQ ID NOS: 20

<210> SEQ ID NO 1
<211> LENGTH: 210
<212> TYPE: PRT
<213> ORGANISM: Brachyspira hyodysenteriae

<400> SEQUENCE: 1

Met Leu Ile Ile Thr Cys Phe Met Ser Ser Ser Leu Phe Pro Leu Ile
1               5                   10                  15

Asp Ala Phe Tyr Leu Ala Pro Lys Val Ile Tyr Asn Phe Asn Asp Ser
            20                  25                  30

Gly Phe Arg Asn Ser Lys Asn Gln Arg Val Met Asn Asn Tyr Leu Gly
        35                  40                  45

Ala Gly Phe Ser Ala Gly Phe Asp Phe Tyr Arg Tyr Gln Arg Asn Ile
    50                  55                  60

Pro Leu Arg Val Glu Leu Glu Tyr Thr Phe Lys Asp Gly Met Thr Gly
65                  70                  75                  80

Asn Tyr His Pro Ala Asn Ile Val Lys Gln Ser Gln His Ser Ile Leu
                85                  90                  95

Ala Ala Ala Tyr Tyr Ser Met His Ile Tyr His Ile Lys Lys Ser Glu
            100                 105                 110

Leu Arg Thr Ile Thr Ala Glu Glu Ile Tyr Ser Arg Thr Pro Ile Met
        115                 120                 125

Ser Leu Tyr Leu Gly Leu Leu Met Gly Thr Lys Ile Asn Ala Asn Thr
    130                 135                 140

Tyr Asp Arg Trp Phe Glu Glu Asn Gly Arg Val Lys Ala Thr Val Thr
145                 150                 155                 160

Val Pro Ser Pro Thr Phe Ala Ile Gly Gly Ala Val Gly Val Asp Ile
                165                 170                 175

Tyr Val Thr Ser Phe Leu Asn Leu Asp Ile Gly Tyr Arg Ile Leu Tyr
            180                 185                 190

Gly Leu Asp Ser Val Leu Ser His Glu Phe Ala Ile Ala Ala Arg Phe
        195                 200                 205

Pro Ile
    210


<210> SEQ ID NO 2
<211> LENGTH: 630
<212> TYPE: DNA
<213> ORGANISM: Brachyspira hyodysenteriae

<400> SEQUENCE: 2
```

-continued

```
atgttaataa taacttgctt tatgagttca tctttgtttc ctctaataga tgcattttat     60

ttagcaccta aagttatata taattttaat gactcaggtt tcagaaatag taaaaatcag    120

agagttatga ataattatct aggagctgga ttttctgcag gatttgactt ctatagatac    180

caaagaaata tacctttgag agtagaatta gagtatactt ttaaagatgg tatgactgga    240

aattatcacc ctgcaaatat agtaaaacaa tctcagcatt ctatattagc agctgcttat    300

tacagcatgc atatatatca tatcaaaaaa agcgaattaa gaactattac agctgaagaa    360

atatatagca gaacgccaat aatgtctcta tatttagggc tgttaatggg tacaaaaata    420

aatgcaaata cttatgatag atggtttgaa gaaaatggaa gagttaaagc tactgtaaca    480

gtgcctagcc ctacatttgc aataggcggt gctgttggag ttgatatata tgttactagc    540

ttccttaact tggatatagg atacagaata ttatatggtt tggatagtgt tttatcacat    600

gaatttgcta tagcagcaag attcccaata                                       630


<210> SEQ ID NO 3
<211> LENGTH: 123
<212> TYPE: PRT
<213> ORGANISM: Brachyspira hyodysenteriae

<400> SEQUENCE: 3

Met Phe Ser Leu Leu Ile Phe Val Ile Ala Ala Cys Lys Ser Thr Pro
1               5                   10                  15

Thr Ser Thr Thr Pro Glu Asp Val Val Ile Ala Asp Asp Pro Ala Pro
            20                  25                  30

Ala Val Ala Glu Glu Glu Pro Lys Pro Glu Glu Val Val Ala Asp Thr
        35                  40                  45

Lys Thr Leu Ala Tyr Gly Ser Glu Glu Leu Tyr Leu Pro Met Asp Thr
    50                  55                  60

Ser Ile Arg Asp Thr Glu Arg Gly Arg Ile Leu Glu Thr Thr Pro Lys
65                  70                  75                  80

Val Ile Phe Lys Phe Val Glu Thr Asn Met Pro Ala Thr Ala Glu Met
                85                  90                  95

Ser Phe Asn Gln Val Val Glu Phe Leu Glu Lys Asn Pro Asn Val Asn
            100                 105                 110

Ile Val Leu Glu Ala His Thr Ser Asn Arg Gly
        115                 120


<210> SEQ ID NO 4
<211> LENGTH: 369
<212> TYPE: DNA
<213> ORGANISM: Brachyspira hyodysenteriae

<400> SEQUENCE: 4

atgtttagtt tattgatctt tgtcatagca gcatgtaaaa gtacgcctac aagtacaaca     60

ccggaagatg tagttatagc agatgatcct gcccctgcag tagcagaaga agaaccaaaa    120

ccagaagaag tagtagctga tactaaaaca ttggcatatg gttctgaaga gctttatcta    180

cctatggata cttctataag agatactgaa agaggaagaa tactagaaac tactccaaaa    240

gtaatattca aatttgtaga gactaatatg cctgcaacag cagaaatgtc attcaatcaa    300

gttgtagagt tttagagaa aaatcctaat gtgaatatag ttttggaagc tcatacaagc    360

aacagaggt                                                              369


<210> SEQ ID NO 5
<211> LENGTH: 189
```

<212> TYPE: PRT
<213> ORGANISM: Brachyspira hyodysenteriae

<400> SEQUENCE: 5

```
Met Leu Leu Met Ser Val Val Ile Ile Ala Ala Ala Cys Lys Ser Ala
1               5                   10                  15

Pro Val Ala Thr Gly Pro Glu Asp Thr Ser Gly Phe Lys Thr Thr Glu
            20                  25                  30

Ala Asn Asn Gln Asn Ala Lys Gly Leu Asn Leu Pro Asp Gly Ala Thr
        35                  40                  45

Val Arg Glu Thr Pro Arg Gly Lys Val Leu Val Leu His Asp Pro Lys
    50                  55                  60

Ser Lys Thr Asp Val Gly Lys Pro Gly Ser Thr Tyr Glu Val Lys Phe
65                  70                  75                  80

Gly Phe Asp Asn Thr Ile Glu Ile Gly Thr Tyr Lys Glu Ala Tyr Asn
                85                  90                  95

Leu Val Tyr Gln Ile Ile Asn Asn Asn Pro Gly Val Arg Ile Met Val
            100                 105                 110

Glu Gly Asn Ser Ser Lys Glu Gly Pro Ala Pro Tyr Asn Tyr Lys Leu
        115                 120                 125

Ser Gln Arg Arg Ser Asp Lys Ser Phe Asn Tyr Ile Ile Lys Leu Gly
    130                 135                 140

Val Glu Asn Ser Lys Leu Leu Lys Asn Ala Phe Gly Glu Ala Leu Pro
145                 150                 155                 160

Glu Tyr Pro Thr Leu Lys Glu Asn Arg Arg Ser Glu Phe Ile Ile Ile
                165                 170                 175

Met Thr Glu Asp Asp Leu Lys Lys Tyr Asn Asp Phe Ala
            180                 185
```

<210> SEQ ID NO 6
<211> LENGTH: 567
<212> TYPE: DNA
<213> ORGANISM: Brachyspira hyodysenteriae

<400> SEQUENCE: 6

```
atgttactta tgtcagtagt tattatagca gctgcatgta aaagtgctcc tgttgcaacc     60

ggtcctgaag acacaagcgg tttcaaaaca acagaagcta ataatcaaaa tgctaaagga    120

cttaacttac ctgacggagc tactgtaaga gaaactccaa gaggtaaagt attagtatta    180

catgatccta aatctaaaac agatgttggt aaacctggtt caacttatga ggtaaaattt    240

ggatttgata atactataga aataggaaca tataaagagg cttataattt agtttatcag    300

ataataaata ataatcctgg tgttagaata atggtggaag gtaattcaag taaagaaggc    360

cctgctcctt ataactataa actatctcag agaagatctg ataaaagctt caattatata    420

ataaaattag gtgtagaaaa cagcaaatta ttaaaaaatg cttttggaga ggctttgcct    480

gaatacccta ctcttaaaga aaatagaaga agcgaattta taataataat gactgaagat    540

gatttgaaaa agtataacga ttttgcc                                        567
```

<210> SEQ ID NO 7
<211> LENGTH: 22
<212> TYPE: DNA
<213> ORGANISM: Artificial
<220> FEATURE:
<223> OTHER INFORMATION: Primer

<400> SEQUENCE: 7

-continued gaaccaaaac cagaagaagt ag 22

<210> SEQ ID NO 8
<211> LENGTH: 21
<212> TYPE: DNA
<213> ORGANISM: Artificial
<220> FEATURE:
<223> OTHER INFORMATION: Primer

<400> SEQUENCE: 8
tttagccctt acaacagaaa g 21

<210> SEQ ID NO 9
<211> LENGTH: 30
<212> TYPE: DNA
<213> ORGANISM: Artificial
<220> FEATURE:
<223> OTHER INFORMATION: Primer

<400> SEQUENCE: 9
ttttacttat gtcagtagtt attatagcag 30

<210> SEQ ID NO 10
<211> LENGTH: 26
<212> TYPE: DNA
<213> ORGANISM: Artificial
<220> FEATURE:
<223> OTHER INFORMATION: Primer

<400> SEQUENCE: 10
aaatcgttat actttttcaa atcatc 26

<210> SEQ ID NO 11
<211> LENGTH: 25
<212> TYPE: DNA
<213> ORGANISM: Artificial
<220> FEATURE:
<223> OTHER INFORMATION: Primer

<400> SEQUENCE: 11
ttcagaaata gtaaaaatca gagag 25

<210> SEQ ID NO 12
<211> LENGTH: 16
<212> TYPE: DNA
<213> ORGANISM: Artificial
<220> FEATURE:
<223> OTHER INFORMATION: Primer

<400> SEQUENCE: 12
ttgggaatct tgctgc 16

<210> SEQ ID NO 13
<211> LENGTH: 34
<212> TYPE: DNA
<213> ORGANISM: Artificial
<220> FEATURE:
<223> OTHER INFORMATION: Primer

<400> SEQUENCE: 13
ttactcgagt ttagtttatt gatctttgtc atag 34

<210> SEQ ID NO 14
<211> LENGTH: 31
<212> TYPE: DNA
<213> ORGANISM: Artificial

<220> FEATURE:
<223> OTHER INFORMATION: Primer

<400> SEQUENCE: 14
actgaattca gtttccctga tatgtacttt c 31

<210> SEQ ID NO 15
<211> LENGTH: 37
<212> TYPE: DNA
<213> ORGANISM: Artificial
<220> FEATURE:
<223> OTHER INFORMATION: Primer

<400> SEQUENCE: 15
aaactcgagt tacttatgtc agtagttatt atagcag 37

<210> SEQ ID NO 16
<211> LENGTH: 30
<212> TYPE: DNA
<213> ORGANISM: Artificial
<220> FEATURE:
<223> OTHER INFORMATION: Primer

<400> SEQUENCE: 16
tcggaattct tggcaaaatc gttatacttt 30

<210> SEQ ID NO 17
<211> LENGTH: 35
<212> TYPE: DNA
<213> ORGANISM: Artificial
<220> FEATURE:
<223> OTHER INFORMATION: Primer

<400> SEQUENCE: 17
ttactcgagt taataataac ttgctttatg agttc 35

<210> SEQ ID NO 18
<211> LENGTH: 27
<212> TYPE: DNA
<213> ORGANISM: Artificial
<220> FEATURE:
<223> OTHER INFORMATION: Primer

<400> SEQUENCE: 18
ctagattcgg tattgggaat cttgctg 27

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
caatttatca gacaatctgt gtg 23

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
tgcctggcag ttccctactc tcg 23

RECOMBINANT OUTER MEMBRANE PROTEINS FROM *BRACHYSPIRA HYODYSENTERIAE* AND USES THEREOF

SEQUENCE LISTING

This application contains a sequence listing in accordance with 37 C.F.R. 1.821-1.825. The sequence listing accompanying this application is hereby incorporated by reference in its entirety and is titled 01-2891-US-1-SUB-SEQ, created on Aug. 9, 2016 and is 9,791 bytes in size.

FIELD OF THE INVENTION

The present invention relates generally to the field of diarrhoeal diseases caused by intestinal spirochaetes. Specifically, the invention relates to a novel approach for inducing systemic and secretory antibody responses against *Brachyspira hyodysenteriae* strains. More specifically, the invention relates to the prevention and/or treatment of infections with *B. hyodysenteriae.*

INTRODUCTION

*Brachyspira hyodysenteriae* is an anaerobic intestinal spirochaete. Infection of pigs with the spirochaete causes swine dysentery (SD), a significant endemic disease of pigs in Australia and worldwide. Swine dysentery is a contagious mucohaemorrhagic diarrhoeal disease, characterised by extensive inflammation and necrosis of the epithelial surface of the large intestine. Economic losses due to swine dysentery result mainly from growth retardation, costs of medication and mortality. Where swine dysentery is established in a piggery, the disease spectrum can vary from being mild, transient or unapparent, to being severe and even fatal. Medication strategies on individual piggeries may mask clinical signs and on some piggeries the disease may go unnoticed, or may only be suspected. Whether or not obvious disease occurs, *B. hyodysenteriae* may persist in infected pigs, or in other reservoir hosts such as rodents, or in the environment. All these sources pose potential for transmission of the disease to uninfected herds. Chickens, geese and other avian and mammalian species are occasionally infected with the spirochaete.

In practice, a number of methods are employed to control swine dysentery, varying from the prophylactic use of antimicrobial agents, to complete destocking of infected herds and prevention of re-entry of infected carrier pigs. All these options are expensive and, if they are to be fully effective, they require the use of sophisticated diagnostic tests to monitor progress.

It is thus an aim of the present invention to make available a novel subunit vaccine, and further a novel subunit vaccine combination, which provides protection against swine dysentery in pigs.

The solution to the above technical problem is achieved by the description and the embodiments characterized in the claims.

Thus, the invention in its different aspects and embodiments is implemented according to the claims.

It is hence an object of this invention to provide a novel use of genes from *B. hyodysenteriae* and of the proteins encoded by those genes. It is a further object of this invention that the genes and the proteins encoded by those genes can be used for therapeutic and diagnostic purposes.

One can use the genes and/or the proteins in a vaccine against *B. hyodysenteriae* and to diagnose *B. hyodysenteriae* infections.

As also mentioned below, the term "protein" and the term "polypeptide" are used interchangeably herein. Preferably, the protein or polypeptide (or proteins or polypeptides), respectively, as described herein, is (or are) recombinant protein(s).

It is an object of this invention to provide a novel use of *B. hyodysenteriae* genes having the nucleotide sequence contained in SEQ ID NOs: 2, 4, and 6, wherein the gene having the nucleotide sequence contained in SEQ ID NO: 2 is also termed OMP10, the gene having the nucleotide sequence contained in SEQ ID NO: 4 is also termed OMP6, and the gene having the nucleotide sequence contained in SEQ ID NO: 6 is also termed OMP7 herein. In particular, it is an object of this invention to provide a novel use of a combination of (i) the *B. hyodysenteriae* gene having the nucleotide sequence contained in SEQ ID NO: 2 and (ii) the *B. hyodysenteriae* gene having the nucleotide sequence contained in SEQ ID NOs: 4 and/or (iii) the *B. hyodysenteriae* gene having the nucleotide sequence contained in SEQ ID NOs: 6. It is also an object of this invention to provide a novel use of nucleotide sequences that are identical to SEQ ID NOs: 2, 4, and 6 where the percentage identity can be at least 95%, 90%, 85%, 80%, 75% and 70% (and every integer from 100 to 70). In particular, it is also an object of this invention to provide a novel use of a combination of (i) the nucleotide sequence that is identical to SEQ ID NO: 2 and (ii) the nucleotide sequence that is identical to SEQ ID NO: 4 and/or (iii) the nucleotide sequence that is identical to SEQ ID NO: 6 where the percentage identity of said nucleotide sequences can be at least 95%, 90%, 85%, 80%, 75% and 70% (and every integer from 100 to 70).

This invention also includes a DNA vaccine or DNA immunogenic composition containing the nucleotide sequence of SEQ ID NOs: 2, 4, and 6 and sequences that are at least 95%, 90%, 85%, 80%, 75% and 70% identical (and every integer from 100 to 70) to these sequences. In particular, this invention also includes a DNA vaccine or DNA immunogenic composition containing a combination of (i) the nucleotide sequence of SEQ ID NO: 2 and (ii) the nucleotide sequence of SEQ ID NO: 4 and/or (iii) the nucleotide sequence of SEQ ID NO: 6 where the percentage identity of said nucleotide sequences can be at least 95%, 90%, 85%, 80%, 75% and 70% (and every integer from 100 to 70). This invention further includes a diagnostic assay containing DNA having the nucleotide sequence of SEQ ID NOs: 2, 4, and 6 and sequences that are at least 95%, 90%, 85%, 80%, 75% and 70% identical (and every integer from 100 to 70) to these sequences. In particular, this invention further includes a diagnostic assay containing the combination of (i) a DNA having the nucleotide sequence of SEQ ID NO: 2 and (ii) a DNA having the nucleotide sequence of SEQ ID NO: 4 and/or (iii) a DNA having the nucleotide sequence of SEQ ID NO: 6 where the percentage identity of said nucleotide sequences can be at least 95%, 90%, 85%, 80%, 75% and 70% (and every integer from 100 to 70).

It is also an object of this invention to provide a novel use of plasmids containing DNA having the sequence of SEQ ID NOs: 2, 4, and 6; and of a cell containing the plasmids which contain DNA having the sequence of SEQ ID NOs: 2, 4, and 6. In particular, it is also an object of this invention to provide a novel use of a combination of (i) a plasmid containing DNA having the sequence of SEQ ID NO: 2 and (ii) a plasmid containing DNA having the sequence of SEQ ID NO: 4 and/or (iii) a plasmid containing DNA having the sequence of SEQ ID NO: 6; and of a combination of (i) a cell containing a plasmid containing DNA having the sequence of SEQ ID NO: 2 and (ii) a cell containing a plasmid containing DNA having the sequence of SEQ ID NO: 4 and/or (iii) a cell containing a plasmid containing DNA having the sequence of SEQ ID NO: 6.

It is further an object of this invention to provide prokaryotic and/or eukaryotic expression vectors containing DNA having the sequence of SEQ ID NOs: 2, 4, and 6. In particular, it is further an object of this invention to provide a combination of (i) a prokaryotic and/or eukaryotic expression vector containing DNA having the sequence of SEQ ID NO: 2 and (ii) a prokaryotic and/or eukaryotic expression vector containing DNA having the sequence of SEQ ID NO: 4 and/or (iii) a prokaryotic and/or eukaryotic expression vector containing DNA having the sequence of SEQ ID NO: 6.

It is an object of this invention to have novel recombinant *B. hyodysenteriae* proteins having the amino acid sequence contained in SEQ ID NOs: 1, 3, and 5. In particular, it is an object of this invention to have a combination of (i) a recombinant *B. hyodysenteriae* protein having the amino acid sequence contained in SEQ ID NO: 1 and (ii) a recombinant *B. hyodysenteriae* protein having the amino acid sequence contained in SEQ ID NO: 3 and/or (iii) a recombinant *B. hyodysenteriae* protein having the amino acid sequence contained in SEQ ID NO: 5.

It is thus another object of this invention to have recombinant proteins that are at least 95%, 90%, 85%, 80%, 75% and 70% homologous (and every integer from 100 to 70) to the sequences contained in SEQ ID NOs: 1, 3, and 5. In particular, it is another object of this invention to have a combination of (i) a recombinant protein that is at least 95%, 90%, 85%, 80%, 75% and 70% homologous (and every integer from 100 to 70) to the sequence SEQ ID NO: 1 and (ii) a recombinant protein that is at least 95%, 90%, 85%, 80%, 75% and 70% homologous (and every integer from 100 to 70) to the sequence of SEQ ID NO: 3 and/or (iii) a recombinant protein that is at least 95%, 90%, 85%, 80%, 75% and 70% homologous (and every integer from 100 to 70) to the sequence of SEQ ID NO: 5.

It is also an object of this invention for a vaccine or immunogenic composition to contain the proteins having the amino acid sequence contained in SEQ ID NOs: 1, 3, and 5, or amino acid sequences that are at least 95%, 90%, 85%, 80%, 75% and 70% homologous (and every integer from 100 to 70) to the sequences contained in SEQ ID NOs: 1, 3, and 5. In particular, it is also an object of this invention for a vaccine or immunogenic composition to contain a combination of (i) a protein having the amino acid sequence SEQ ID NO: 1, or an amino acid sequence that is at least 95%, 90%, 85%, 80%, 75% and 70% homologous (and every integer from 100 to 70) to the sequence of SEQ ID NO: 1 and (ii) a protein having the amino acid sequence SEQ ID NO: 3, or an amino acid sequence that is at least 95%, 90%, 85%, 80%, 75% and 70% homologous (and every integer from 100 to 70) to the sequence of SEQ ID NO: 3 and/or (iii) a protein having the amino acid sequence SEQ ID NO: 5, or an amino acid sequence that is at least 95%, 90%, 85%, 80%, 75% and 70% homologous (and every integer from 100 to 70) to the sequence of SEQ ID NO: 5.

It is a further aspect of this invention to have a diagnostic kit containing one or more recombinant proteins having a sequence contained in SEQ ID NOs: 1, 3, and 5 or that are at least 95%, 90%, 85%, 80%, 75% and 70% homologous to the sequences contained in SEQ ID NOs: 1, 3, and 5. In particular, it is a further aspect of this invention to have a diagnostic kit containing a combination of (i) a recombinant protein having the sequence of SEQ ID NO: 1 or having a sequence that is at least 95%, 90%, 85%, 80%, 75% and 70% homologous to the sequence of SEQ ID NO: 1 and (ii) a recombinant protein having the sequence of SEQ ID NO: 3 or having a sequence that is at least 95%, 90%, 85%, 80%, 75% and 70% homologous to the sequence of SEQ ID NO: 3 and/or (iii) a recombinant protein having the sequence of SEQ ID NO: 5 or having a sequence that is at least 95%, 90%, 85%, 80%, 75% and 70% homologous to the sequence of SEQ ID NO: 5.

It is another aspect of this invention to use nucleotide sequences which encode the proteins having the amino acid sequence contained in SEQ ID NOs: 1, 3, and 5, and encode the amino acid sequences that are at least 95%, 90%, 85%, 80%, 75% and 70% homologous (and every integer from 100 to 70) to the sequences contained in SEQ ID NOs: 1, 3, and 5. In particular, it is another aspect of this invention to use a combination of (i) a nucleotide sequence which encodes the protein having the amino acid sequence SEQ ID NO: 1, or encodes the amino acid sequence that is at least 95%, 90%, 85%, 80%, 75% and 70% homologous (and every integer from 100 to 70) to the sequence of SEQ ID NO: 1 and (ii) a nucleotide sequence which encodes the protein having the amino acid sequence SEQ ID NO: 3, or encodes the amino acid sequence that is at least 95%, 90%, 85%, 80%, 75% and 70% homologous (and every integer from 100 to 70) to the sequence of SEQ ID NO: 3 and/or (iii) a nucleotide sequence which encodes the protein having the amino acid sequence SEQ ID NO: 5, or encodes the amino acid sequence that is at least 95%, 90%, 85%, 80%, 75% and 70% homologous (and every integer from 100 to 70) to the sequence of SEQ ID NO: 5.

The invention also covers the use of plasmids, and eukaryotic and prokaryotic expression vectors, and DNA vaccines which contain DNA having a sequence which encodes a protein having the amino acid sequence contained in SEQ ID NOs: 1, 3, and 5, and encode amino acid sequences that are at least 95%, 90%, 85%, 80%, 75% and 70% homologous (and every integer from 100 to 70) to the sequences contained in SEQ ID NOs: 1, 3, and 5. The use of cells which contain these plasmids and cells which contain these expression vectors are included in this invention. In particular, the invention also covers the use of a combination of (i) a plasmid, or a eukaryotic or prokaryotic expression vector, or a DNA vaccine which contains DNA having a sequence which encodes the protein having the amino acid sequence SEQ ID NO: 1, or encodes an amino acid sequence that is at least 95%, 90%, 85%, 80%, 75% and 70% homologous (and every integer from 100 to 70) to the sequence of SEQ ID NO: 1 and (ii) a plasmid, or a eukaryotic or prokaryotic expression vector, or a DNA vaccine which contains DNA having a sequence which encodes the protein having the amino acid sequence SEQ ID NO: 3, or encodes an amino acid sequence that is at least 95%, 90%, 85%, 80%, 75% and 70% homologous (and every integer from 100 to 70) to the sequence of SEQ ID NO: 3 and/or (iii) a plasmid, or a eukaryotic or prokaryotic expression vector, or a DNA vaccine which contains DNA having a sequence which encodes the protein having the amino acid sequence SEQ ID NO: 5, or encodes an amino acid sequence that is at least 95%, 90%, 85%, 80%, 75% and 70% homologous (and every integer from 100 to 70) to the sequence of SEQ ID NO: 5. Accordingly, also the use of a combination of (a) a cell containing the plasmid or expression vector of (i) and (b) a cell containing the plasmid or expression vector of (ii) and/or (c) a cell containing the plasmid or expression vector of (iii) is included in this invention.

This invention includes monoclonal antibodies that bind to proteins having an amino acid sequence contained in SEQ ID NOs: 1, 3, and 5 or bind to proteins that are at least 95%, 90%, 85%, 80%, 75% and 70% homologous (and every integer from 100 to 70) to the sequences contained in SEQ ID NOs: 1, 3, and 5. In particular, this invention includes a combination of (i) a monoclonal antibody that binds to the protein having the amino acid sequence SEQ ID NO: 1 or binds to a protein that is at least 95%, 90%, 85%, 80%, 75% and 70% homologous (and every integer from 100 to 70) to the sequence of SEQ ID NO: 1 and (ii) a monoclonal antibody that binds to the protein having the amino acid sequence SEQ ID NO: 3 or binds to a protein that is at least 95%, 90%, 85%, 80%, 75% and 70% homologous (and every integer from 100 to 70) to the sequence of SEQ ID NO: 3 and/or (iii) a monoclonal antibody that binds to the protein having the amino acid sequence SEQ ID NO: 5 or binds to a protein that is at least 95%, 90%, 85%, 80%, 75% and 70% homologous (and every integer from 100 to 70) to the sequence of SEQ ID NO: 5.

Diagnostic kits containing the monoclonal antibodies that bind to proteins having an amino acid sequence contained in SEQ ID NOs: 1, 3, and 5 or bind to proteins that are at least 95%, 90%, 85%, 80%, 75% and 70% homologous (and every integer from 100 to 70) to the sequences contained in SEQ ID NOs: 1, 3, and 5 are included in this invention. In particular, diagnostic kits containing a combination of (i) a monoclonal antibody that binds to the protein having the amino acid sequence SEQ ID NO: 1 or binds to a protein that is at least 95%, 90%, 85%, 80%, 75% and 70% homologous (and every integer from 100 to 70) to the sequence of SEQ ID NO: 1 and (ii) a monoclonal antibody that binds to the protein having the amino acid sequence SEQ ID NO: 3 or binds to a protein that is at least 95%, 90%, 85%, 80%, 75% and 70% homologous (and every integer from 100 to 70) to the sequence of SEQ ID NO: 3 and/or (iii) a monoclonal antibody that binds to the protein having the amino acid sequence SEQ ID NO: 5 or binds to a protein that is at least 95%, 90%, 85%, 80%, 75% and 70% homologous (and every integer from 100 to 70) to the sequence of SEQ ID NO: 5 are included in this invention.

These diagnostic kits can detect the presence of *B. hyodysenteriae* in an animal.

The term "animal", as described herein, is in particular directed to any mammal and bird; more preferably, chicken, goose, duck, turkey, parakeet, dog, cat, hamster, gerbil, rabbit, ferret, horse, cow, sheep, pig, monkey, and human.

The invention also contemplates the method of preventing or treating an infection of *B. hyodysenteriae* in an animal by administering to an animal a DNA vaccine containing one or more nucleotide sequences listed in SEQ ID NOs: 2, 4, and 6 or sequences that are at least 95%, 90%, 85%, 80%, 75% and 70% identical (and every integer from 100 to 70) to these sequences. In particular, the invention also contemplates the method of preventing or treating an infection of *B. hyodysenteriae* in an animal by administering to an animal a DNA vaccine containing a combination of (i) the nucleotide sequence of SEQ ID NO: 2 or a sequence that is at least 95%, 90%, 85%, 80%, 75% and 70% identical (and every integer from 100 to 70) to this sequence and (ii) the nucleotide sequence of SEQ ID NO: 4 or a sequence that is at least 95%, 90%, 85%, 80%, 75% and 70% identical (and every integer from 100 to 70) to this sequence and/or (iii) the nucleotide sequence of SEQ ID NO: 6 or a sequence that is at least 95%, 90%, 85%, 80%, 75% and 70% identical (and every integer from 100 to 70) to this sequence.

This invention also covers a method of preventing or treating an infection of *B. hyodysenteriae* in an animal by administering to an animal a vaccine containing one or more proteins having the amino acid sequence containing in SEQ ID NOs: 1, 3, and 5 or sequences that are at least 95%, 90%, 85%, 80%, 75% and 70% homologous (and every integer from 100 to 70) to these sequences. In particular, this invention also covers a method of preventing or treating an infection of *B. hyodysenteriae* in an animal by administering to an animal a vaccine containing a combination of (i) a protein having the amino acid sequence of SEQ ID NO: 1 or a sequence that is at least 95%, 90%, 85%, 80%, 75% and 70% homologous (and every integer from 100 to 70) to this sequence and (ii) a protein having the amino acid sequence of SEQ ID NO: 3 or a sequence that is at least 95%, 90%, 85%, 80%, 75% and 70% homologous (and every integer from 100 to 70) to this sequence and/or (iii) a protein having the amino acid sequence of SEQ ID NO: 5 or a sequence that is at least 95%, 90%, 85%, 80%, 75% and 70% homologous (and every integer from 100 to 70) to this sequence. The animal is preferably any mammal and bird; more preferably, chicken, goose, duck, turkey, parakeet, dog, cat, hamster, gerbil, rabbit, ferret, horse, cow, sheep, pig, monkey, and human.

The invention also contemplates the method of generating an immune response in an animal by administering to an animal an immunogenic composition containing one or more nucleotide sequences listed in SEQ ID NOs: 2, 4, and 6 or sequences that are at least 95%, 90%, 85%, 80%, 75% and 70% identical (and every integer from 100 to 70) to these sequences. In particular, the invention also contemplates the method of generating an immune response in an animal by administering to an animal an immunogenic composition containing a combination of (i) the nucleotide sequence of SEQ ID NO: 2 or a sequence that is at least 95%, 90%, 85%, 80%, 75% and 70% identical (and every integer from 100 to 70) to this sequence and (ii) the nucleotide sequence of SEQ ID NO: 4 or a sequence that is at least 95%, 90%, 85%, 80%, 75% and 70% identical (and every integer from 100 to 70) to this sequence and/or (iii) the nucleotide sequence of SEQ ID NO: 6 or a sequence that is at least 95%, 90%, 85%, 80%, 75% and 70% identical (and every integer from 100 to 70) to this sequence.

This invention also covers a method of generating an immune response in an animal by administering to an animal an immunogenic composition containing one or more proteins having the amino acid sequence containing in SEQ ID NOs: 1, 3, and 5 or sequences that are at least 95%, 90%, 85%, 80%, 75% and 70% homologous (and every integer from 100 to 70) to these sequences. In particular, this invention also covers a method of generating an immune response in an animal by administering to an animal an immunogenic composition containing a combination of (i) a protein having the amino acid sequence of SEQ ID NO: 1 or a sequence that are at least 95%, 90%, 85%, 80%, 75% and 70% homologous (and every integer from 100 to 70) to this sequence and (ii) a protein having the amino acid sequence of SEQ ID NO: 3 or a sequence that are at least 95%, 90%, 85%, 80%, 75% and 70% homologous (and every integer from 100 to 70) to this sequence and/or (iii) a protein having the amino acid sequence of SEQ ID NO: 5 or a sequence that are at least 95%, 90%, 85%, 80%, 75% and 70% homologous (and every integer from 100 to 70) to this sequence. The animal is preferably any mammal and bird; more preferably, chicken, goose, duck, turkey, parakeet, dog, cat, hamster, gerbil, rabbit, ferret, horse, cow, sheep, pig, monkey, and human.

With regard to all combinations and their uses as mentioned above, the invention is thus in particular directed to a combination of (i) and (ii), a combination of (i) and (iii), a combination of (i) and (ii) and (iii).

With regard to the vaccines, immunogenic compositions, expression vectors, proteins, kits, and monoclonal antibodies, as mentioned above, the term "combination" in particular relates to a single composition (formulation), in particular a pharmaceutical or diagnostic composition, containing the respective components (i) and (ii) and/or (iii) or also may relate to two or three separate compositions (formulations) or substances, each comprising or consisting of a single of the respective components (i) and (ii) and/or (iii) to be administered or used conjointly. Within the meaning of the present invention, the term "administered or used conjointly" in particular refers to the administration or use of the components (i) and (ii) and/or (iii) simultaneously in one composition, or simultaneously in different compositions, or sequentially.

With regard to the use of genes, use of plasmids, use of nucleotide sequences, use of cells, use of expression vectors, and use of DNA vaccines, as mentioned above, the term "combination" in particular relates to both modes where two or three separate compositions (formulations) or substances, each comprising or consisting of a single of the respective components (i) and (ii) and/or (iii) are used in combination or where they are provided as a mixture. According to the present invention, "used in combination" does not only refer to exactly the same use timing of the components (i) and (ii) and/or (iii). As long as the the components (i) and (ii) and/or (iii) are used during a single use schedule, both simultaneous and separate uses thereof can be referred to as "used in combination". When they are used separately, the use of the components (i) and (ii) and/or (iii) may be done in any order.

With regard to the methods of preventing or treating an infection of *B. Hyodysenteriae* and the methods of generating an immune response in an animal, as mentioned above, the term "combination" in particular relates to both modes where two or three separate compositions (formulations), each comprising a single of the respective components (i) and (ii) and/or (iii) are administered in combination or where they are administered as a mixture (compounding agent). According to the present invention, "administered in combination" does not only refer to exactly the same administration timing of the components (i) and (ii) and/or (iii). As long as the components (i) and (ii) and/or (iii) are used during a single administration schedule, both simultaneous and separate administrations can be referred to as "administered in combination". When they are administered separately, the administration of the components (i) and (ii) and/or (iii) may be done in any order.

DETAILED SUMMARY OF INVENTION

The articles "a" and "an" are used herein to refer to one or to more than one (i.e., to at least one) of the grammatical object of the article. By way of example, "an element" means one element or more than one element.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

An animal can be any mammal or bird. Examples of mammals include dog, cat, hamster, gerbil, rabbit, ferret, horse, cow, sheep, pig, monkey, and human. Examples of birds include chicken, goose, duck, turkey, and parakeet.

The term "conserved residue" refers to an amino acid that is a member of a group of amino acids having certain common properties. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (Schulz, Georg E., and R. Heiner Schirmer, *Principles of protein structure*. Springer Science & Business Media, 2013). According to such analyses, groups of amino acids may be defined where amino acids within a group exchange preferentially with each other, and therefore resemble each other most in their impact on the overall protein structure (Schulz, Georg E., and R. Heiner Schirmer, *Principles of protein structure*. Springer Science & Business Media, 2013). Examples of amino acid groups defined in this manner include: (i) a positively-charged group containing Lys, Arg and His, (ii) a negatively-charged group containing Glu and Asp, (iii) an aromatic group containing Phe, Tyr and Trp, (iv) a nitrogen ring group containing His and Trp, (v) a large aliphatic nonpolar group containing Val, Leu and De, (vi) a slightly-polar group containing Met and Cys, (vii) a small-residue group containing Ser, Thr, Asp, Asn, Gly, Ala, Glu, Gln and Pro, (viii) an aliphatic group containing Val, Leu, De, Met and Cys, and (ix) a small, hydroxyl group containing Ser and Thr.

A "fusion protein" or "fusion polypeptide" refers to a chimeric protein as that term is known in the art and may be constructed using methods known in the art. In many examples of fusion proteins, there are two different polypeptide sequences, and in certain cases, there may be more. The polynucleotide sequences encoding the fusion protein may be operably linked in frame so that the fusion protein may be translated correctly. A fusion protein may include polypeptide sequences from the same species or from different species. In various embodiments, the fusion polypeptide may contain one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides containing a glutathione S-transferase tag (GST-tag), histidine tag (His-tag), an immunoglobulin domain or an immunoglobulin binding domain.

The term "isolated polypeptide" refers to a polypeptide, in certain embodiments prepared from recombinant DNA or RNA, or of synthetic origin or natural origin, or some combination thereof, which (1) is not associated with proteins that it is normally found with in nature, (2) is separated from the cell in which it normally occurs, (3) is free of other proteins from the same cellular source, (4) is expressed by a cell from a different species, or (5) does not occur in nature. It is possible for an isolated polypeptide exist but not qualify as a purified polypeptide.

The term "isolated nucleic acid" and "isolated polynucleotide" refers to a polynucleotide whether genomic DNA, cDNA, mRNA, tRNA, rRNA, IRNA, or a polynucleotide obtained from a cellular organelle (such as mitochondria and chloroplast), or whether from synthetic origin, which (1) is not associated with the cell in which the "isolated nucleic acid" is found in nature, or (2) is operably linked to a polynucleotide to which it is not linked in nature. It is possible for an isolated polynucleotide exist but not qualify as a purified polynucleotide.

The term "nucleic acid" and "polynucleotide" refers to a polymeric form of nucleotides, either ribonucleotides or deoxyribonucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "nucleic acid of the invention" and "polynucleotide of the invention" refers to a nucleic acid encoding a polypeptide of the invention. A polynucleotide of the invention may comprise all, or a portion of, a subject nucleic acid sequence; a nucleotide sequence at least 60%, 70%, 80%, 90%, 95%, 96%, 97%, 98% or 99% identical to a subject nucleic acid sequence (and every integer between 60 and 100); a nucleotide sequence that hybridizes under stringent conditions to a subject nucleic acid sequence; nucleotide sequences encoding polypeptides that are functionally equivalent to polypeptides of the invention; nucleotide sequences encoding polypeptides at least about 60%, 70%, 80%, 85%, 90%, 95%, 98%, 99% homologous or identical with a subject amino acid sequence (and every integer between 60 and 100); nucleotide sequences encoding polypeptides having an activity of a polypeptide of the invention and having at least about 60%, 70%, 80%, 85%, 90%, 95%, 98%, 99% or more homology or identity with a subject amino acid sequence (and every integer between 60 and 100); nucleotide sequences that differ by 1 to about 2, 3, 5, 7, 10, 15, 20, 30, 50, 75 or more nucleotide substitutions, additions or deletions, such as allelic variants, of a subject nucleic acid sequence; nucleic acids derived from and evolutionarily related to a subject nucleic acid sequence; and complements of, and nucleotide sequences resulting from the degeneracy of the genetic code, for all of the foregoing and other nucleic acids of the invention. Nucleic acids of the invention also include homologs, e.g., orthologs and paralogs, of a subject nucleic acid sequence and also variants of a subject nucleic acid sequence which have been codon optimized for expression in a particular organism (e.g., host cell).

The term "operably linked", when describing the relationship between two nucleic acid regions, refers to a juxtaposition wherein the regions are in a relationship permitting them to function in their intended manner. For example, a control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

The term "polypeptide", and the terms "protein" and "peptide" which are used interchangeably herein, refers to a polymer of amino acids. Exemplary polypeptides include gene products, naturally-occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In certain embodiments, a fragment may comprise a domain having the desired biological activity, and optionally additional amino acids on one or both sides of the domain, which additional amino acids may number from 5, 10, 15, 20, 30, 40, 50, or up to 100 or more residues. Further, fragments can include a sub-fragment of a specific region, which sub-fragment retains a function of the region from which it is derived. In another embodiment, a fragment may have immunogenic properties.

The term "polypeptide of the invention" refers to a polypeptide containing a subject amino acid sequence, or an equivalent or fragment thereof. Polypeptides of the invention include polypeptides containing all or a portion of a subject amino acid sequence; a subject amino acid sequence with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% homologous to a subject amino acid sequence (and every integer between 60 and 100); and functional fragments thereof. Polypeptides of the invention also include homologs, e.g., orthologs and paralogs, of a subject amino acid sequence.

It is also possible to modify the structure of the polypeptides of the invention for such purposes as enhancing therapeutic or prophylactic efficacy, or stability (e.g., ex vivo shelf life, resistance to proteolytic degradation in vivo, etc.). Such modified polypeptides, when designed to retain at least one activity of the naturally-occurring form of the protein, are considered "functional equivalents" of the polypeptides described in more detail herein. Such modified polypeptides may be produced, for instance, by amino acid substitution, deletion, or addition, which substitutions may consist in whole or part by conservative amino acid substitutions.

For instance, it is reasonable to expect that an isolated conservative amino acid substitution, such as replacement of a leucine with an isoleucine or valine, an aspartate with a glutamate, a threonine with a serine, will not have a major affect on the biological activity of the resulting molecule. Whether a change in the amino acid sequence of a polypeptide results in a functional homolog may be readily determined by assessing the ability of the variant polypeptide to produce a response similar to that of the wild-type protein. Polypeptides in which more than one replacement has taken place may readily be tested in the same manner.

The term "purified" refers to an object species that is the predominant species present (i.e., on a molar basis it is more abundant than any other individual species in the composition). A "purified fraction" is a composition wherein the object species is at least about 50 percent (on a molar basis) of all species present. In making the determination of the purity or a species in solution or dispersion, the solvent or matrix in which the species is dissolved or dispersed is usually not included in such determination; instead, only the species (including the one of interest) dissolved or dispersed are taken into account. Generally, a purified composition will have one species that is more than about 80% of all species present in the composition, more than about 85%, 90%, 95%, 99% or more of all species present. The object species may be purified to essential homogeneity (contaminant species cannot be detected in the composition by conventional detection methods) wherein the composition is essentially a single species. A skilled artisan may purify a polypeptide of the invention using standard techniques for protein purification in light of the teachings herein. Purity of a polypeptide may be determined by a number of methods known to those of skill in the art, including for example, amino-terminal amino acid sequence analysis, gel electrophoresis, mass-spectrometry analysis and the methods described herein.

The terms "recombinant protein" or "recombinant polypeptide" refer to a polypeptide which is produced by recombinant DNA techniques. An example of such techniques includes the case when DNA encoding the expressed protein is inserted into a suitable expression vector which is in turn used to transform a host cell to produce the protein or polypeptide encoded by the DNA.

The term "regulatory sequence" is a generic term used throughout the specification to refer to polynucleotide sequences, such as initiation signals, enhancers, regulators and promoters, that are necessary or desirable to affect the expression of coding and non-coding sequences to which they are operably linked. Exemplary regulatory sequences are described in Goeddel; Gene Expression Technology: Methods in Enzymology, Academic Press, San Diego, Calif. (1990), and include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase (e.g., Pho5), the promoters of the yeast α-mating factors, the polyhedron promoter of the baculovirus system and other sequences known to control the expression of genes of prokaryotic or eukaryotic cells or their viruses, and various combinations thereof. The nature and use of such control sequences may differ depending upon the host organism. In prokaryotes, such regulatory sequences generally include promoter, ribosomal binding site, and transcription termination sequences. The term "regulatory sequence" is intended to include, at a minimum, components whose presence may influence expression, and may also include additional components whose presence is advantageous, for example, leader sequences and fusion partner sequences. In certain embodiments, transcription of a polynucleotide sequence is under the control of a promoter sequence (or other regulatory sequence) which controls the expression of the polynucleotide in a cell-type in which expression is intended. It will also be understood that the polynucleotide can be under the control of regulatory sequences which are the same or different from those sequences which control expression of the naturally-occurring form of the polynucleotide.

The term "sequence homology" refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids or nucleotides occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

The term "soluble" as used herein with reference to a polypeptide of the invention or other protein, means that upon expression in cell culture, at least some portion of the polypeptide or protein expressed remains in the cytoplasmic fraction of the cell and does not fractionate with the cellular debris upon lysis and centrifugation of the lysate. Solubility of a polypeptide may be increased by a variety of art recognized methods, including fusion to a heterologous amino acid sequence, deletion of amino acid residues, amino acid substitution (e.g., enriching the sequence with amino acid residues having hydrophilic side chains), and chemical modification (e.g., addition of hydrophilic groups).

The solubility of polypeptides may be measured using a variety of art recognized techniques, including, dynamic light scattering to determine aggregation state, UV absorption, centrifugation to separate aggregated from non-aggregated material, and SDS gel electrophoresis (e.g., the amount of protein in the soluble fraction is compared to the amount of protein in the soluble and insoluble fractions combined). When expressed in a host cell, the polypeptides of the invention may be at least about 1%, 2%, 5%, 10%, 20%, 30%, 40%, 50%, 60%, 70%, 80%, 90% or more soluble, e.g., at least about 1%, 2%, 5%, 10%, 20%, 30%, 40%, 50%, 60%, 70%, 80%, 90% or more of the total amount of protein expressed in the cell is found in the cytoplasmic fraction. In certain embodiments, a one liter culture of cells expressing a polypeptide of the invention will produce at least about 0.1, 0.2, 0.5, 1, 2, 5, 10, 20, 30, 40, 50 milligrams of more of soluble protein. In an exemplary embodiment, a polypeptide of the invention is at least about 10% soluble and will produce at least about 1 milligram of protein from a one liter cell culture.

The term "specifically hybridizes" refers to detectable and specific nucleic acid binding. Polynucleotides, oligonucleotides and nucleic acids of the invention selectively hybridize to nucleic acid strands under hybridization and wash conditions that minimize appreciable amounts of detectable binding to nonspecific nucleic acids. Stringent conditions may be used to achieve selective hybridization conditions as known in the art and discussed herein. Generally, the nucleic acid sequence identity between the polynucleotides, oligonucleotides, and nucleic acids of the invention and a nucleic acid sequence of interest will be at least 30%, 40%, 50%, 60%, 70%, 80%, 85%, 90%, 95%, 98%, 99%, or more (and every integer between 30 and 100). In certain instances, hybridization and washing conditions are performed under stringent conditions according to conventional hybridization procedures and as described further herein.

The terms "stringent conditions" or "stringent hybridization conditions" refer to conditions which promote specific hybridization between two complementary polynucleotide strands so as to form a duplex. Stringent conditions may be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of a polynucleotide sequence hybridizes to a perfectly matched complementary strand. In certain cases it may be desirable to increase the stringency of the hybridization conditions to be about equal to the Tm for a particular duplex.

A variety of techniques for estimating the Tm are available. Typically, G-C base pairs in a duplex are estimated to contribute about 3° C. to the Tm, while A-T base pairs are estimated to contribute about 2° C., up to a theoretical maximum of about 80-100° C.

However, more sophisticated models of Tm are available in which G-C stacking interactions, solvent effects, the desired assay temperature and the like are taken into account. For example, probes can be designed to have a dissociation temperature (Td) of approximately 60° C., using the formula: Td=(((3×#GC)+(2×#AT))×37)−562)/#bp)−5; where #GC, #AT, and #bp are the number of guanine-cytosine base pairs, the number of adenine-thymine base pairs, and the number of total base pairs, respectively, involved in the formation of the duplex.

Hybridization may be carried out in 5×SSC, 4×SSC, 3×SSC, 2×SSC, 1×SSC or 0.2×SSC for at least about 1 hour, 2 hours, 5 hours, 12 hours, or 24 hours. The temperature of the hybridization may be increased to adjust the stringency of the reaction, for example, from about 25° C. (room temperature), to about 45° C., 50° C., 55° C., 60° C., or 65° C. The hybridization reaction may also include another agent affecting the stringency, for example, hybridization conducted in the presence of 50% formamide increases the stringency of hybridization at a defined temperature.

The hybridization reaction may be followed by a single wash step, or two or more wash steps, which may be at the same or a different salinity and temperature. For example, the temperature of the wash may be increased to adjust the stringency from about 25° C. (room temperature), to about 45° C., 50° C., 55° C., 60° C., 65° C., or higher. The wash step may be conducted in the presence of a detergent, e.g., 0.1 or 0.2% SDS. For example, hybridization may be followed by two wash steps at 65° C. each for about 20 minutes in 2×SSC, 0.1% SDS, and optionally two additional wash steps at 65° C. each for about 20 minutes in 0.2×SSC, 0.1% SDS.

Exemplary stringent hybridization conditions include overnight hybridization at 65° C. in a solution containing 50% formamide, 10×Denhardt (0.2% Ficoll, 0.2% polyvinylpyrrolidone, 0.2% bovine serum albumin) and 200 μg/ml of denatured carrier DNA, e.g., sheared salmon sperm DNA, followed by two wash steps at 65° C. each for about 20 minutes in 2×SSC, 0.1% SDS, and two wash steps at 65° C. each for about 20 minutes in 0.2×SSC, 0.1% SDS.

Hybridization may consist of hybridizing two nucleic acids in solution, or a nucleic acid in solution to a nucleic acid attached to a solid support, e.g., a filter. When one nucleic acid is on a solid support, a prehybridization step may be conducted prior to hybridization. Prehybridization may be carried out for at least about 1 hour, 3 hours or 10 hours in the same solution and at the same temperature as the hybridization solution (without the complementary polynucleotide strand).

Appropriate stringency conditions are known to those skilled in the art or may be determined experimentally by the skilled artisan. See, for example, Current Protocols in Molecular Biology, John Wiley & Sons, N.Y. (1989), 6.3.1-12.3.6; Sambrook et al., 1989, Molecular Cloning, A Laboratory Manual, Cold Spring Harbor Press, N.Y.; S. Agrawal (ed.) Methods in Molecular Biology, volume 20; Tijssen (1993) Laboratory Techniques in Biochemistry and Molecular Biology—Hybridization With Nucleic Acid Probes, e.g., part I chapter 2 "Overview of principles of hybridization and the strategy of nucleic acid probe assays", Elsevier, New York; and Tibanyenda, N. et al., Eur. J. Biochem. 139:19 (1984) and Ebel, S. et al., Biochem. 31:12083 (1992).

The term "vector" refers to a nucleic acid capable of transporting another nucleic acid to which it has been linked. One type of vector which may be used in accord with the invention is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The nucleic acids of the invention may be used as diagnostic reagents to detect the presence or absence of the target DNA or RNA sequences to which they specifically bind, such as for determining the level of expression of a nucleic acid of the invention. In one aspect, the present invention contemplates a method for detecting the presence of a nucleic acid of the invention or a portion thereof in a sample, the method of the steps of: (a) providing an oligonucleotide at least eight nucleotides in length, the oligonucleotide being complementary to a portion of a nucleic acid of the invention; (b) contacting the oligonucleotide with a sample containing at least one nucleic acid under conditions that permit hybridization of the oligonucleotide with a nucleic acid of the invention or a portion thereof; and (c) detecting hybridization of the oligonucleotide to a nucleic acid in the sample, thereby detecting the presence of a nucleic acid of the invention or a portion thereof in the sample. In another aspect, the present invention contemplates a method for detecting the presence of a nucleic acid of the invention or a portion thereof in a sample, by (a) providing a pair of single stranded oligonucleotides, each of which is at least eight nucleotides in length, complementary to sequences of a nucleic acid of the invention, and wherein the sequences to which the oligonucleotides are complementary are at least ten nucleotides apart; and (b) contacting the oligonucleotides with a sample containing at least one nucleic acid under hybridization conditions; (c) amplifying the nucleotide sequence between the two oligonucleotide primers; and (d) detecting the presence of the amplified sequence, thereby detecting the presence of a nucleic acid of the invention or a portion thereof in the sample.

In another aspect of the invention, the polynucleotide of the invention is provided in an expression vector containing a nucleotide sequence encoding a polypeptide of the invention and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered.

An expression vector containing the polynucleotide of the invention can then be used as a pharmaceutical agent to treat an animal infected with *B. hyodysenteriae* or as a vaccine (also a pharmaceutical agent) to prevent an animal from being infected with *B. hyodysenteriae*, or to reduce the symptoms and course of the disease if the animal does become infected. One manner of using an expression vector as a pharmaceutical agent is to administer a nucleic acid vaccine to the animal at risk of being infected or to the animal after being infected. Nucleic acid vaccine technology is well-described in the art. Some descriptions can be found in U.S. Pat. No. 6,562,376 (Hooper et al.); U.S. Pat. No. 5,589,466 (Felgner, et al.); U.S. Pat. No. 6,673,776 (Felgner, et al.); and U.S. Pat. No. 6,710,035 (Felgner, et al.). Nucleic acid vaccines can be injected into muscle or intradermally, can be electroporated into the animal (see WO 01/23537, King et al.; and WO 01/68889, Malone et al.), via lipid compositions (see U.S. Pat. No. 5,703,055, Felgner, et al), or other mechanisms known in the art field.

Expression vectors can also be transfected into bacteria which can be administered to the target animal to induce an immune response to the protein encoded by the nucleotides of this invention contained on the expression vector. The expression vector can contain eukaryotic expression sequences such that the nucleotides of this invention are transcribed and translated in the host animal. Alternatively, the expression vector can be transcribed in the bacteria and then translated in the host animal. The bacteria used as a carrier of the expression vector should be attenuated but still invasive. One can use *Shigella* spp., *Salmonella* spp., *Escherichia* spp., and *Aeromonas* spp., just to name a few, that have been attenuated but still invasive. Examples of these methods can be found in U.S. Pat. No. 5,824,538 (Branstrom et al); U.S. Pat. No. 5,877,159 (Powell, et al.); U.S. Pat. No. 6,150,170 (Powell, et al.); U.S. Pat. No. 6,500,419 (Hone, et al.); and U.S. Pat. No. 6,682,729 (Powell, et al.).

Alternatively, the polynucleotides of this invention can be placed in certain viruses which act a vector. Viral vectors can either express the proteins of this invention on the surface of the virus, or carry polynucleotides of this invention into an animal cell where the polynucleotide is transcribed and translated into a protein. The animal infected with the viral vectors can develop an immune response to the proteins encoded by the polynucleotides of this invention. Thereby one can alleviate or prevent an infection by *B. hyodysenteriae* in the animal which received the viral vectors. Examples of viral vectors can be found U.S. Pat. No. 5,283,191 (Morgan et al.); U.S. Pat. No. 5,554,525 (Sondermeijer et al) and U.S. Pat. No. 5,712,118 (Murphy).

The polynucleotide of the invention may be used to cause expression and over-expression of a polypeptide of the invention in cells propagated in culture, e.g. to produce proteins or polypeptides, including fusion proteins or polypeptides.

This invention pertains to a host cell transfected with a recombinant gene in order to express a polypeptide of the invention. The host cell may be any prokaryotic or eukaryotic cell. For example, a polypeptide of the invention may be expressed in bacterial cells, such as *E. coli*, insect cells (baculovirus), yeast, plant, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Alternatively, the nucleotide sequence may be altered to optimize expression in the host cell, yet the protein produced would have high homology to the originally encoded protein. Other methods suitable for maximizing expression of the polypeptide will be known to those in the art.

The present invention further pertains to methods of producing the polypeptides of the invention. For example, a host cell transfected with an expression vector encoding a polypeptide of the invention may be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated.

A cell culture includes host cells, media and other byproducts. Suitable media for cell culture are well known in the art. The polypeptide may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of a polypeptide of the invention.

Thus, a nucleotide sequence encoding all or a selected portion of polypeptide of the invention, may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant polypeptides of the invention by microbial means or tissue-culture technology.

Suitable vectors for the expression of a polypeptide of the invention include plasmids of the types: pTrcHis-derived plasmids, pET-derived plasmids, pBR322-derived plasmids, pEMBL-derived plasmids, pEX-derived plasmids, pBTac-derived plasmids and pUC-derived plasmids for expression in prokaryotic cells, such as *E. coli*. The various methods employed in the preparation of the plasmids and transformation of host organisms are well known in the art. For other suitable expression systems for both prokaryotic and eukaryotic cells, as well as general recombinant procedures, see *Molecular Cloning, A Laboratory Manual,* 2nd Ed., ed. by Sambrook, Fritsch and Maniatis (Cold Spring Harbor Laboratory Press, 1989) Chapters 16 and 17.

Coding sequences for a polypeptide of interest may be incorporated as a part of a fusion gene including a nucleotide sequence encoding a different polypeptide. The present invention contemplates an isolated polynucleotide containing a nucleic acid of the invention and at least one heterologous sequence encoding a heterologous peptide linked in frame to the nucleotide sequence of the nucleic acid of the invention so as to encode a fusion protein containing the heterologous polypeptide. The heterologous polypeptide may be fused to (a) the C-terminus of the polypeptide of the invention, (b) the N-terminus of the polypeptide of the invention, or (c) the C-terminus and the N-terminus of the polypeptide of the invention. In certain instances, the heterologous sequence encodes a polypeptide permitting the detection, isolation, solubilization and/or stabilization of the polypeptide to which it is fused. In still other embodiments, the heterologous sequence encodes a polypeptide such as a poly His tag, myc, HA, GST, protein A, protein G, calmodulin-binding peptide, thioredoxin, maltose-binding protein, poly arginine, poly His-Asp, FLAG, a portion of an immunoglobulin protein, and a transcytosis peptide.

Fusion expression systems can be useful when it is desirable to produce an immunogenic fragment of a polypeptide of the invention. For example, the VP6 capsid protein of rotavirus may be used as an immunologic carrier protein for portions of polypeptide, either in the monomeric form or in the form of a viral particle. The nucleic acid sequences corresponding to the portion of a polypeptide of the invention to which antibodies are to be raised may be incorporated into a fusion gene construct which includes coding sequences for a late vaccinia virus structural protein to produce a set of recombinant viruses expressing fusion proteins comprising a portion of the protein as part of the virion. The Hepatitis B surface antigen may also be utilized in this role as well. Similarly, chimeric constructs coding for fusion proteins containing a portion of a polypeptide of the invention and the poliovirus capsid protein may be created to enhance immunogenicity (see, for example, EP Publication NO: 0259149; and Evans et al., (1989) *Nature* 339:385; Huang et al., (1988) *J. Virol.* 62:3855; and Schlienger et al., (1992) *J. Virol.* 66:2).

Fusion proteins may facilitate the expression and/or purification of proteins. For example, a polypeptide of the invention may be generated as a glutathione-S-transferase (GST) fusion protein. Such GST fusion proteins may be used to simplify purification of a polypeptide of the invention, such as through the use of glutathione-derivatized matrices (see, for example, *Current Protocols in Molecular Biology*, eds. Ausubel et al., (N.Y.: John Wiley & Sons, 1991)). In another embodiment, a fusion gene coding for a purification leader sequence, such as a poly-(His)/enterokinase cleavage site sequence at the N-terminus of the desired portion of the recombinant protein, may allow purification of the expressed fusion protein by affinity chromatography using a $Ni^{2+}$ metal resin. The purification leader sequence may then be subsequently removed by treatment with enterokinase to provide the purified protein (e.g., see Hochuli et al., (1987) *J. Chromatography* 411: 177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed to generate a chimeric gene sequence (see, for example, *Current Protocols in Molecular Biology*, eds. Ausubel et al., John Wiley & Sons: 1992).

In other embodiments, the invention provides for nucleic acids of the invention immobilized onto a solid surface, including, plates, microtiter plates, slides, beads, particles, spheres, films, strands, precipitates, gels, sheets, tubing, containers, capillaries, pads, slices, etc. The nucleic acids of the invention may be immobilized onto a chip as part of an array. The array may contain one or more polynucleotides of the invention as described herein. In one embodiment, the chip contains one or more polynucleotides of the invention as part of an array of polynucleotide sequences from the same pathogenic species as such polynucleotide(s).

In a preferred form of the invention there is provided isolated *B. hyodysenteriae* polypeptides as herein described, and also the polynucleotide sequences encoding these polypeptides. More desirably the *B. hyodysenteriae* polypeptides are provided in substantially purified form.

Preferred polypeptides of the invention will have one or more biological properties (e.g., in vivo, in vitro or immunological properties) of the native full-length polypeptide. Non-functional polypeptides are also included within the scope of the invention because they may be useful, for example, as antagonists of the functional polypeptides. The biological properties of analogues, fragments, or derivatives relative to wild type may be determined, for example, by means of biological assays.

Polypeptides, including analogues, fragments and derivatives, can be prepared synthetically (e.g., using the well known techniques of solid phase or solution phase peptide synthesis). Preferably, solid phase synthetic techniques are employed. Alternatively, the polypeptides of the invention can be prepared using well known genetic engineering techniques, as described infra. In yet another embodiment, the polypeptides can be purified (e.g., by immunoaffinity purification) from a biological fluid, such as but not limited to plasma, faeces, serum, or urine from animals, including, but not limited to, pig, chicken, goose, duck, turkey, parakeet, human, monkey, dog, cat, horse, hamster, gerbil, rabbit, ferret, horse, cattle, and sheep. An animal can be any mammal or bird.

The *B. hyodysenteriae* polypeptide analogues include those polypeptides having the amino acid sequence, wherein one or more of the amino acids are substituted with another amino acid which substitutions do not substantially alter the biological activity of the molecule.

According to the invention, the polypeptides of the invention produced recombinantly or by chemical synthesis and fragments or other derivatives or analogues thereof, including fusion proteins, may be used as an immunogen to generate antibodies that recognize the polypeptides.

A molecule is "antigenic" when it is capable of specifically interacting with an antigen recognition molecule of the immune system, such as an immunoglobulin (antibody) or T cell antigen receptor. An antigenic amino acid sequence contains at least about 5, and preferably at least about 10, amino acids. An antigenic portion of a molecule can be the portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, $F(ab')_2$ and F(v) (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds an antigen.

Exemplary antibody molecules are intact immunoglobulin molecules, substantially intact immunoglobulin molecules and those portions of an immunoglobulin molecule that contain the paratope, including those portions known in the art as Fab, Fab', $F(ab')_2$ and F(v), which portions are preferred for use in the therapeutic methods described herein.

Fab and $F(ab')_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from $F(ab')_2$ portions followed by reduction with mercaptoethanol of the disulfide bonds linking the two heavy chain portions, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "adjuvant" refers to a compound or mixture that enhances the immune response to an antigen. An adjuvant can serve as a tissue depot that slowly releases the antigen and also as a lymphoid system activator that non-specifically enhances the immune response [Hood et al., in *Immunology, p.* 384, Second Ed., Benjamin/Cummings, Menlo Park, Calif. (1984)]. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminium hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Various procedures known in the art may be used for the production of polyclonal antibodies to the polypeptides of the invention. For the production of antibody, various host animals can be immunised by injection with the polypeptide of the invention, including but not limited to rabbits, mice, rats, sheep, goats, etc. In one embodiment, a polypeptide of the invention can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacilie Calmette-Guerin) and *Corynebacterium parvum.*

For preparation of monoclonal antibodies directed toward a polypeptide of the invention, any technique that provides for the production of antibody molecules by continuous cell lines in culture may be used. These include but are not limited to the hybridoma technique originally developed by Kohler et al., (1975) *Nature,* 256:495-497, the trioma technique, the human B-cell hybridoma technique [Kozbor et al., (1983) *Immunology Today,* 4:72], and the EBV-hybridoma technique to produce human monoclonal antibodies [Cole et al., (1985) in *Monoclonal Antibodies and Cancer Therapy*, pp. 77-96, Alan R. Liss, Inc.]. Immortal, antibody-producing cell lines can be created by techniques other than fusion, such as direct transformation of B lymphocytes with oncogenic DNA, or transfection with Epstein-Barr virus. See, e.g., U.S. Pat. Nos. 4,341,761; 4,399,121; 4,427,783; 4,444,887; 4,451,570; 4,466,917; 4,472,500; 4,491,632; and 4,493,890.

In an additional embodiment of the invention, monoclonal antibodies can be produced in germ-free animals utilising recent technology. According to the invention, chicken or swine antibodies may be used and can be obtained by using chicken or swine hybridomas or by transforming B cells with EBV virus in vitro. In fact, according to the invention, techniques developed for the production of "chimeric antibodies" [Morrison et al., (1984) *J. Bacteriol.,* 159-870; Neuberger et al., (1984) *Nature,* 312:604-608; Takeda et al., (1985) *Nature,* 314:452-454] by splicing the genes from a mouse antibody molecule specific for a polypeptide of the invention together with genes from an antibody molecule of appropriate biological activity can be used; such antibodies are within the scope of this invention. Such chimeric antibodies are preferred for use in therapy of intestinal diseases or disorders (described infra), since the antibodies are much less likely than xenogenic antibodies to induce an immune response, in particular an allergic response, themselves.

According to the invention, techniques described for the production of single chain antibodies (U.S. Pat. No. 4,946,778) can be adapted to produce single chain antibodies specific for an polypeptide of the invention. An additional embodiment of the invention utilises the techniques described for the construction of Fab expression libraries [Huse et al., (1989) *Science,* 246:1275-1281] to allow rapid and easy identification of monoclonal Fab fragments with the desired specificity for a polypeptide of the invention.

Antibody fragments, which contain the idiotype of the antibody molecule, can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA, "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention. For example, to select antibodies that recognise a specific epitope of a polypeptide of the invention, one may assay generated hybridomas for a product that binds to a fragment of a polypeptide of the invention containing such epitope.

The invention also covers diagnostic and prognostic methods to detect the presence of *B. hyodysenteriae* using a polypeptide of the invention and/or antibodies which bind to the polypeptide of the invention and kits useful for diagnosis and prognosis of *B. hyodysenteriae* infections.

Diagnostic and prognostic methods will generally be conducted using a biological sample obtained from an animal, such as chicken or swine. A "sample" refers to an animal's tissue or fluid suspected of containing a *Brachyspira* species, such as *B. hyodysenteriae*, or its polynucleotides or its polypeptides. Examples of such tissue or fluids include, but not limited to, plasma, serum, fecal material, urine, lung, heart, skeletal muscle, stomach, intestines, and in vitro cell culture constituents.

The invention provides methods for detecting the presence of a polypeptide of the invention in a sample, with the following steps: (a) contacting a sample suspected of containing a polypeptide of the invention with an antibody (preferably bound to a solid support) that specifically binds to the polypeptide of the invention under conditions which allow for the formation of reaction complexes comprising the antibody and the polypeptide of the invention; and (b) detecting the formation of reaction complexes comprising the antibody and polypeptide of the invention in the sample, wherein detection of the formation of reaction complexes indicates the presence of the polypeptide of the invention in the sample.

Preferably, the antibody used in this method is derived from an affinity-purified polyclonal antibody, and more preferably a monoclonal antibody. In addition, it is preferable for the antibody molecules used herein be in the form of Fab, Fab', $F(ab')_2$ or F(v) portions or whole antibody molecules.

Particularly preferred methods for detecting *B. hyodysenteriae* based on the above method include enzyme linked immunosorbent assays, radioimmunoassays, immunoradiometric assays and immunoenzymatic assays, including sandwich assays using monoclonal and/or polyclonal antibodies.

Three such procedures that are especially useful utilise either polypeptide of the invention (or a fragment thereof) labelled with a detectable label, antibody $Ab_1$ labelled with a detectable label, or antibody $Ab_2$ labelled with a detectable label. The procedures may be summarized by the following equations wherein the asterisk indicates that the particle is labelled and "AA" stands for the polypeptide of the invention:

$$AA^{*}+Ab_1=AA^{*}Ab_1 \qquad \text{A.}$$

$$AA+Ab^{*}_1=AA\ Ab_1^{*} \qquad \text{B.}$$

$$AA+Ab_1+Ab_2^{*}=AB_1AA\ Ab_2^{*} \qquad \text{C.}$$

The procedures and their application are all familiar to those skilled in the art and accordingly may be utilised within the scope of the present invention. The "competitive" procedure, Procedure A, is described in U.S. Pat. Nos. 3,654,090 and 3,850,752. Procedure B is representative of well-known competitive assay techniques. Procedure C, the "sandwich" procedure, is described in U.S. Pat. Nos. RE 31,006 and 4,016,043. Still other procedures are known, such as the "double antibody" or "DASP" procedure, and can be used.

In each instance, the polypeptide of the invention form complexes with one or more antibody(ies) or binding partners and one member of the complex is labelled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This reaction is because $Ab_1$, raised in one mammalian species, has been used in another species as an antigen to raise the antibody, $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary antibody, and $Ab_2$ will be referred to as a secondary or anti-$Ab_1$ antibody.

The labels most commonly employed for these studies are radioactive elements, enzymes, chemicals that fluoresce when exposed to ultraviolet light, and others. Examples of fluorescent materials capable of being utilised as labels include fluorescein, rhodamine and auramine. A particular detecting material is anti-rabbit antibody prepared in goats and conjugated with fluorescein through an isothiocyanate. Examples of preferred isotope include $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. The radioactive label can be detected by any of the currently available counting procedures. While many enzymes can be used, examples of preferred enzymes are peroxidase, β-glucuronidase, β-D-glucosidase, β-D-galactosidase, urease, glucose oxidase plus peroxidase and alkaline phosphatase. Enzyme are conjugated to the selected particle by reaction with bridging molecules such as carbodiimides, diisocyanates, glutaraldehyde and the like. Enzyme labels can be detected by any of the presently utilized colorimetric, spectrophotometric, fluorospectrophotometric, amperometric or gasometric techniques. U.S. Pat. Nos. 3,654,090; 3,850,752; and 4,016,043 are referred to by way of example for their disclosure of alternate labelling material and methods.

The invention also provides a method of detecting antibodies to a polypeptide of the invention in biological samples, using the following steps: (a) providing a polypeptide of the invention or a fragment thereof; (b) incubating a biological sample with said polypeptide of the invention under conditions which allow for the formation of an antibody-antigen complex; and (c) determining whether an antibody-antigen complex with the polypeptide of the invention is formed.

In another embodiment of the invention there are provided in vitro methods for evaluating the level of antibodies to a polypeptide of the invention in a biological sample using the following steps: (a) detecting the formation of reaction complexes in a biological sample according to the method noted above; and (b) evaluating the amount of reaction complexes formed, which amount of reaction complexes corresponds to the level of polypeptide of the invention in the biological sample.

Further there are provided in vitro methods for monitoring therapeutic treatment of a disease associated with *B. hyodysenteriae* in an animal host by evaluating, as describe above, the levels of antibodies to a polypeptide of the invention in a series of biological samples obtained at different time points from an animal host undergoing such therapeutic treatment.

The present invention further provides methods for detecting the presence or absence of *B. hyodysenteriae* in a biological sample by: (a) bringing the biological sample into contact with a polynucleotide probe or primer of polynucleotide of the invention under suitable hybridizing conditions; and (b) detecting any duplex formed between the probe or primer and nucleic acid in the sample.

According to one embodiment of the invention, detection of *B. hyodysenteriae* may be accomplished by directly amplifying polynucleotide sequences from biological sample, using known techniques and then detecting the presence of polynucleotide of the invention sequences.

In one form of the invention, the target nucleic acid sequence is amplified by PCR and then detected using any of the specific methods mentioned above. Other useful diagnostic techniques for detecting the presence of polynucleotide sequences include, but are not limited to: 1) allele-specific PCR; 2) single stranded conformation analysis; 3) denaturing gradient gel electrophoresis; 4) RNase protection assays; 5) the use of proteins which recognize nucleotide mismatches, such as the *E. coli* mutS protein; 6) allele-specific oligonucleotides; and 7) fluorescent in situ hybridisation.

In addition to the above methods polynucleotide sequences may be detected using conventional probe technology. When probes are used to detect the presence of the desired polynucleotide sequences, the biological sample to be analysed, such as blood or serum, may be treated, if desired, to extract the nucleic acids. The sample polynucleotide sequences may be prepared in various ways to facilitate detection of the target sequence; e.g. denaturation, restriction digestion, electrophoresis or dot blotting. The targeted region of the sample polynucleotide sequence usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Sample polynucleotide sequences and probes are incubated under conditions that promote stable hybrid formation of the target sequence in the probe with the putative desired polynucleotide sequence in the sample. Preferably, high stringency conditions are used in order to prevent false positives.

Detection, if any, of the resulting hybrid is usually accomplished by the use of labelled probes. Alternatively, the probe may be unlabeled, but may be detectable by specific binding with a ligand that is labelled, either directly or indirectly. Suitable labels and methods for labelling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labelled moiety.

It is also contemplated within the scope of this invention that the nucleic acid probe assays of this invention may employ a cocktail of nucleic acid probes capable of detecting the desired polynucleotide sequences of this invention. Thus, in one example to detect the presence of polynucleotide sequences of this invention in a cell sample, more than one probe complementary to a polynucleotide sequences is employed and in particular the number of different probes is alternatively 2, 3, or 5 different nucleic acid probe sequences.

The polynucleotide sequences described herein (preferably in the form of probes) may also be immobilised to a solid phase support for the detection of *Brachyspira* species, including but not limited to *B. hyodysenteriae, B. intermedia, B. alvinipulli, B. aalborgi, B. innocens, B. murdochii*, and *B. pilosicoli*. Alternatively the polynucleotide sequences described herein will form part of a library of DNA molecules that may be used to detect simultaneously a number of different genes from *Brachyspira* species, such as *B. hyodysenteriae*. In a further alternate form of the invention polynucleotide sequences described herein together with other polynucleotide sequences (such as from other bacteria or viruses) may be immobilised on a solid support in such a manner permitting identification of the presence of a *Brachyspira* species, such as *B. hyodysenteriae* and/or any of the other polynucleotide sequences bound onto the solid support.

Techniques for producing immobilised libraries of DNA molecules have been described in the art. Generally, most prior art methods describe the synthesis of single-stranded nucleic acid molecule libraries, using for example masking techniques to build up various permutations of sequences at the various discrete positions on the solid substrate. U.S. Pat. No. 5,837,832 describes an improved method for producing DNA arrays immobilised to silicon substrates based on very large scale integration technology. In particular, U.S. Pat. No. 5,837,832 describes a strategy called "tiling" to synthesize specific sets of probes at spatially defined locations on a substrate that may be used to produced the immobilised DNA libraries of the present invention. U.S. Pat. No. 5,837,832 also provides references for earlier techniques that may also be used. Thus polynucleotide sequence probes may be synthesised in situ on the surface of the substrate.

Alternatively, single-stranded molecules may be synthesised off the solid substrate and each pre-formed sequence applied to a discrete position on the solid substrate. For example, polynucleotide sequences may be printed directly onto the substrate using robotic devices equipped with either pins or pizo electric devices.

The library sequences are typically immobilised onto or in discrete regions of a solid substrate. The substrate may be porous to allow immobilisation within the substrate or substantially non-porous, in which case the library sequences are typically immobilised on the surface of the substrate. The solid substrate may be made of any material to which polypeptides can bind, either directly or indirectly. Examples of suitable solid substrates include flat glass, silicon wafers, mica, ceramics and organic polymers such as plastics, including polystyrene and polymethacrylate. It may also be possible to use semi-permeable membranes such as nitrocellulose or nylon membranes, which are widely available. The semi-permeable membranes may be mounted on a more robust solid surface such as glass. The surfaces may optionally be coated with a layer of metal, such as gold, platinum or other transition metal.

Preferably, the solid substrate is generally a material having a rigid or semi-rigid surface. In preferred embodiments, at least one surface of the substrate will be substantially flat, although in some embodiments it may be desirable to physically separate synthesis regions for different polymers with, for example, raised regions or etched trenches. It is also preferred that the solid substrate is suitable for the high density application of DNA sequences in discrete areas of typically from 50 to 100 μm, giving a density of 10000 to 40000 dots/cm$^{-2}$.

The solid substrate is conveniently divided up into sections. This may be achieved by techniques such as photoetching, or by the application of hydrophobic inks, for example teflon-based inks (Cel-line, USA).

Discrete positions, in which each different member of the library is located may have any convenient shape, e.g., circular, rectangular, elliptical, wedge-shaped, etc.

Attachment of the polynucleotide sequences to the substrate may be by covalent or non-covalent means. The polynucleotide sequences may be attached to the substrate via a layer of molecules to which the library sequences bind. For example, the polynucleotide sequences may be labelled with biotin and the substrate coated with avidin and/or streptavidin. A convenient feature of using biotinylated polynucleotide sequences is that the efficiency of coupling to the solid substrate can be determined easily. Since the polynucleotide sequences may bind only poorly to some solid substrates, it is often necessary to provide a chemical interface between the solid substrate (such as in the case of glass) and the nucleic acid sequences. Examples of suitable chemical interfaces include hexaethylene glycol. Another example is the use of polylysine coated glass, the polylysine then being chemically modified using standard procedures to introduce an affinity ligand. Other methods for attaching molecules to the surfaces of solid substrate by the use of coupling agents are known in the art, see for example WO98/49557.

Binding of complementary polynucleotide sequences to the immobilised nucleic acid library may be determined by a variety of means such as changes in the optical characteristics of the bound polynucleotide sequence (i.e. by the use of ethidium bromide) or by the use of labelled nucleic acids, such as polypeptides labelled with fluorophores. Other detection techniques that do not require the use of labels include optical techniques such as optoacoustics, reflectometry, ellipsometry and surface plasmon resonance (see WO97/49989).

Thus, the present invention provides a solid substrate having immobilized thereon at least one polynucleotide of the present invention, preferably two or more different polynucleotide sequences of the present invention.

The present invention also can be used as a prophylactic or therapeutic, which may be utilised for the purpose of stimulating humoral and cell mediated responses in animals, such as chickens and swine, thereby providing protection against colonisation with *Brachyspira* species, including but not limited to *B. hyodysenteriae, B. suanatina, B. intermedia, B. alvinipulli, B. aalborgi, B. innocens, B. murdochii*, and *B. pilosicoli*. Natural infection with a *Brachyspira* species, such as *B. hyodysenteriae* induces circulating antibody titres against the proteins described herein. Therefore, the amino acid sequences described herein or parts thereof, have the potential to form the basis of a systemically or orally administered prophylactic or therapeutic to provide protection against intestinal spirochaetosis.

Accordingly, in one embodiment the present invention provides the amino acid sequences described herein or fragments thereof or antibodies that bind the amino acid sequences or the polynucleotide sequences described herein in a therapeutically effective amount admixed with a pharmaceutically acceptable carrier, diluent, or excipient.

The phrase "therapeutically effective amount" is used herein to mean an amount sufficient to reduce by at least about 15%, preferably by at least 50%, more preferably by at least 90%, and most preferably prevent, a clinically significant deficit in the activity, function and response of the animal host. Alternatively, a therapeutically effective amount is sufficient to cause an improvement in a clinically significant condition in the animal host.

The phrase "pharmaceutically acceptable" refers to molecular entities and compositions that are physiologically tolerable and do not typically produce an allergic or similarly untoward reaction, such as gastric upset and the like, when administered to an animal. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, *Remington's Pharmaceutical Sciences,* 18th Ed., Mack Publishing Co., Easton, Pa., (1990).

In a more specific form of the invention there are provided pharmaceutical compositions comprising therapeutically effective amounts of the amino acid sequences described herein or an analogue, fragment or derivative product thereof or antibodies thereto together with pharmaceutically acceptable diluents, preservatives, solubilizes, emulsifiers, adjuvants and/or carriers. Such compositions include diluents of various buffer content (e.g., Tris-HCl, acetate, phosphate), pH and ionic strength and additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as polylactic acid, polyglycolic acid, etc. or into liposomes. Hyaluronic acid may also be used. Such compositions may influence the physical state, stability, rate of in vivo release, and rate of in vivo clearance of the present proteins and derivatives. See, e.g., Martin, *Remington's Pharmaceutical Sciences,* 18th Ed. (1990, Mack Publishing Co., Easton, Pa. 18042) pages 1435-1712 that are herein incorporated by reference. The compositions may be prepared in liquid form, or may be in dried powder, such as lyophilised form.

Alternatively, the polynucleotides of the invention can be optimized for expression in plants (e.g., corn). The plant may be transformed with plasmids containing the optimized polynucleotides. Then the plant is grown, and the proteins of the invention are expressed in the plant, or the plant-optimized version is expressed. The plant is later harvested, and the section of the plant containing the proteins of the invention is processed into feed for the animal. This animal feed will impart immunity against *B. hyodysenteriae* when eaten by the animal. Examples of prior art detailing these methods can be found in U.S. Pat. No. 5,914,123 (Arntzen, et al.); U.S. Pat. No. 6,034,298 (Lam, et at); and U.S. Pat. No. 6,136,320 (Arntzen, et al.).

It will be appreciated that pharmaceutical compositions provided accordingly to the invention may be administered by any means known in the art. Preferably, the pharmaceutical compositions for administration are administered by injection, orally, or by the pulmonary, or nasal route. The amino acid sequences described herein or antibodies derived therefrom are more preferably delivered by intravenous, intraarterial, intraperitoneal, intramuscular, or subcutaneous routes of administration. Alternatively, the amino acid sequence described herein or antibodies derived therefrom, properly formulated, can be administered by nasal or oral administration.

Also encompassed by the present invention is the use of polynucleotide sequences of the invention, as well as antisense and ribozyme polynucleotide sequences hybridizable to a polynucleotide sequence encoding an amino acid sequence according to the invention, for manufacture of a medicament for modulation of a disease associated *B. hyodysenteriae.*

Polynucleotide sequences encoding antisense constructs or ribozymes for use in therapeutic methods are desirably administered directly as a naked nucleic acid construct. Uptake of naked nucleic acid constructs by bacterial cells is enhanced by several known transfection techniques, for example those including the use of transfection agents. Example of these agents include cationic agents (for example calcium phosphate and DEAE-dextran) and lipofectants. Typically, nucleic acid constructs are mixed with the transfection agent to produce a composition.

Alternatively the antisense construct or ribozymes may be combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular, oral or transdermal administration. The routes of administration described are intended only as a guide since a skilled practitioner will be able to determine readily the optimum route of administration and any dosage for any particular animal and condition.

The invention also includes kits for screening animals suspected of being infected with a *Brachyspira* species, such as *B. hyodysenteriae* or to confirm that an animal is infected with a *Brachyspira* species, such as *B. hyodysenteriae*. In a further embodiment of this invention, kits suitable for use by a specialist may be prepared to determine the presence or absence of *Brachyspira* species, including but not limited to *B. hyodysenteriae, B. suanatina, B. intermedia, B. alvinipulli, B. aalborgi, B. innocens, B. murdochii*, and *B. pilosicoli* in suspected infected animals or to quantitatively measure a *Brachyspira* species, including but not limited to *B. hyodysenteriae, B. suanatina, B. intermedia, B. alvinipulli, B. aalborgi* and *B. pilosicoli* infection. In accordance with the testing techniques discussed above, such kits can contain at least a labelled version of one of the amino acid sequences described herein or its binding partner, for instance an antibody specific thereto, and directions depending upon the method selected, e.g., “competitive,” “sandwich,” “DASP” and the like. Alternatively, such kits can contain at least a polynucleotide sequence complementary to a portion of one of the polynucleotide sequences described herein together with instructions for its use. The kits may also contain peripheral reagents such as buffers, stabilizers, etc.

Accordingly, a test kit for the demonstration of the presence of a *Brachyspira* species, including but not limited to *B. hyodysenteriae, B. suanatina, B. intermedia, B. alvinipulli, B. aalborgi, B. innocens, B. murdochii*, and *B. pilosicoli*, may contain the following:

SEQUENCE REQUIREMENTS (a) a predetermined amount of at least one labelled immunochemically reactive component obtained by the direct or indirect attachment of one of the amino acid sequences described herein or a specific binding partner thereto, to a detectable label;

(b) other reagents; and (c) directions for use of said kit.

More specifically, the diagnostic test kit may contain:

(a) a known amount of one of the amino acid sequences described herein as described above (or a binding partner) generally bound to a solid phase to form an immunosorbent, or in the alternative, bound to a suitable tag, or there are a plural of such end products, etc;

(b) if necessary, other reagents; and (c) directions for use of said test kit.

In a further variation, the test kit may contain:

(a) a labelled component which has been obtained by coupling one of the amino acid sequences described herein to a detectable label;

(b) one or more additional immunochemical reagents of which at least one reagent is a ligand or an immobilized ligand, which ligand is selected from the group consisting of:

(i) a ligand capable of binding with the labelled component (a);

(ii) a ligand capable of binding with a binding partner of the labelled component (a);

(iii) a ligand capable of binding with at least one of the component(s) to be determined; or (iv) a ligand capable of binding with at least one of the binding partners of at least one of the component(s) to be determined; and (c) directions for the performance of a protocol for the detection and/or determination of one or more components of an immunochemical reaction between one of the amino acid sequences described herein and a specific binding partner thereto.

In a more specific aspect, the invention is based on the surprising finding that a particular recombinant polypeptide provides protection against swine dysentery in pigs.

In one aspect the invention is thus directed to a recombinant polypeptide comprising or consisting of a sequence that is at least 70%, preferably at least 80%, more preferably at least 90%, still more preferably at least 95% or in particular 100% identical to the sequence of SEQ ID NO: 1. In the following, the recombinant polypeptide is also termed “recombinant polypeptide of the invention”.

The term “recombinant polypeptide”, as used herein, in particular refers to a protein molecule which is expressed from a recombinant DNA molecule.

It is further understood that the term “recombinant polypeptide consisting of a sequence” in particular also concerns any cotranslational and/or posttranslational modification or modifications of the sequence effected by the cell in which the polypeptide is expressed. Thus, the term “recombinant polypeptide consisting of a sequence”, as described herein, is also directed to the sequence having one or more modifications effected by the cell in which the polypeptide is expressed, in particular modifications of amino acid residues effected in the protein biosynthesis and/or protein processing, preferably selected from the group consisting of glycosylations, phosphorylations, and acetylations.

The term “recombinant polypeptide consisting of a sequence” in particular also comprises any protein tag attached to the respective polypeptide, such as any peptide sequence genetically grafted to the respective recombinant protein for a technical purpose, in particular an affinity tag appended to the protein so that the protein can be purified from its crude biological source using an affinity technique.

The term “recombinant polypeptide consisting of a sequence Y” thus particularly relates to a recombinant protein having the sequence Y and additionally an affinity tag attached, preferably appended, to the sequence Y, wherein the affinity tag is in particular selected from group consisting of polyhistidine tag, chitin binding protein (CBP), maltose binding protein (MBP), and glutahione-S-transferase (GST). The polyhisitdinge tag is preferably an amino acid motif consisting of a least five histidine residues at the N- or C-terminus of the protein, wherein a hexa histidine-tag (6×His-tag) is particularly preferred.

Preferably, the recombinant polypeptide of the invention is produced or obtainable by a baculovirus expression system, in particular in cultured insect cells.

According to another aspect, the invention concerns an immunogenic composition containing a recombinant polypeptide comprising or consisting of a sequence that is at least 70%, preferably at least 80%, more preferably at least 90%, still more preferably at least 95% or in particular 100% identical to the sequence of SEQ ID NO: 1. In the following, the immunogenic composition is also termed "immunogenic composition of the invention".

It is understood, that the immunogenic composition of the invention, or the vaccine composition of the invention, respectively, in particular contains a therapeutically effective amount of said recombinant polypeptide and/or of the further recombinant polypeptide(s) mentioned hereinafter, wherein the immunogenic composition preferably contains 5 μg to 5 mg, preferably 50 μg to 2 mg, or more preferably 100 μg to 1 mg, or most preferably 250 μg to 750 μg of each of the recombinant proteins contained therein. Preferably, the same amount is also used for the preparation of a medicament, as described herein, or is administered in the method of generating an immune response to *Brachyspira hyodysenteriae* described herein.

In a particular preferred aspect, the immunogenic composition of the invention further contains a recombinant polypeptide comprising or consisting of a sequence that is at least 70%, preferably at least 80%, more preferably at least 90%, still more preferably at least 95% or in particular 100% identical to the sequence of SEQ ID NO: 3 and/or a recombinant polypeptide comprising or consisting of a sequence that is at least 70% identical to the sequence of SEQ ID NO: 5, and wherein preferably said further recombinant polypeptide or said further recombinant polypeptides is or are produced or obtainable by a baculovirus expression system, in particular in cultured insect cells.

Thus, the immunogenic composition of the invention preferably further contains a recombinant polypeptide comprising or consisting of a sequence that is at least 70%, preferably at least 80%, more preferably at least 90%, still more preferably at least 95% or in particular 100% identical to the sequence of SEQ ID NO: 3,
or the immunogenic composition of the invention preferably further contains a recombinant polypeptide comprising or consisting of a sequence that is at least 70%, preferably at least 80%, more preferably at least 90%, still more preferably at least 95% or in particular 100% identical to the sequence of SEQ ID NO: 5.

In particular, the immunogenic composition of the invention further preferably contains (i) a recombinant polypeptide comprising or consisting of a sequence that is at least 70%, preferably at least 80%, more preferably at least 90%, still more preferably at least 95% or in particular 100% identical to the sequence of SEQ ID NO: 3
and (ii) a recombinant polypeptide comprising or consisting of a sequence that is at least 70%, preferably at least 80%, more preferably at least 90%, still more preferably at least 95% or in particular 100% identical to the sequence of SEQ ID NO: 5.

As used herein, the term "immunogenic composition" in particular refers to a composition that will elicit an immune response in an animal that has been exposed to the composition. An immune response may include induction of antibodies and/or induction of a T-cell response.

Usually, an "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number or severity of, or lack of one or more of the symptoms associated with the infection of the pathogen, in a reduced bacterial persistence, in a reduction of the overall bacterial load and/or in a reduction of bacterial excretion.

Thus, an "immune response" in particular means but is not limited to the development in a subset of a cellular and/or antibody-mediated immune response to the composition or vaccine of interest.

In one aspect, the immunogenic composition of the invention is preferably a vaccine or medicament.

In another aspect, the invention relates to the recombinant polypeptide of the invention or the immunogenic composition of the invention for use as a medicament Preferably, the medicament as mentioned herein is a vaccine.

In a further aspect, the invention is directed to the recombinant polypeptide of the invention or the immunogenic composition of the invention for use in a method for treating or preventing clinical signs caused by *Brachyspira hyodysenteriae* or for use in a method for treating or preventing a disease caused by *Brachyspira hyodysenteriae*.

As used herein the term "disease caused by *Brachyspira hyodysenteriae*" in particular relates to dysentery caused by *Brachyspira hyodysenteriae*, more particular to swine dysentery.

The term "clinical signs caused by *Brachyspira hyodysenteriae*" in particular relates to any clinical sign selected from mucus and/or blood in feces (dysentery), diarrhoea, weight loss, lesions in the large intestine, spirochaete (*Brachyspira hyodysenteriae*) in the large intestine.

The term "prevention" or "preventing" or "treatment" or "treating", respectively, as used herein, means, but is not limited to a process which includes the administration of a *Brachyspira hyodysenteriae* antigen, namely of the recombinant polypeptide of the invention or the immunogenic composition of the invention, to an animal, wherein said *Brachyspira hyodysenteriae* antigen, when administered to said animal elicits or is able to elicit an immune response in said animal against *Brachyspira hyodysenteriae* antigen.

Altogether, such administration results in reduction of the clinical signs of a disease caused by *Brachyspira hyodysenteriae* or of symptoms associated with *Brachyspira hyodysenteriae* infection, respectively.

More specifically, the term "prevention" or "preventing, as used herein, means generally a process of prophylaxis in which an animal is exposed to the recombinant polypeptide of the invention or the immunogenic composition of the invention prior to the induction or onset of the disease process ((swine) dysentery).

Also, more specifically, the term "treatment" or "treating" as used herein generally relates to a reduction in the severity of an existing disease or condition, including complete curing of a disease as well as amelioration or alleviation of said disease.

Herein, "reduction of the clinical signs of a disease caused by *Brachyspira hyodysenteriae*" or "reduction of symptoms associated with *Brachyspira hyodysenteriae* infection", respectively, means, but is not limited to, reducing the number of infected subjects in a group, reducing or eliminating the number of subjects exhibiting clinical symptoms of infection, or reducing the severity of any clinical symptoms that are present in the subjects, in comparison to wild-type infection. For example, it should refer to any reduction of pathogen load, pathogen shedding, reduction in pathogen transmission, or reduction of any clinical sign symptomatic of *Brachyspira hyodysenteriae* infection, in particular selected from mucus and/or blood in feces (dysentery), diarrhoea, weight loss, lesions in the large intestine, spirochaete (*Brachyspira hyodysenteriae*) in the large intestine. Preferably these clinical signs are reduced in subjects receiving the recombinant polypeptide of the invention or the immunogenic composition of the invention by at least 10% in comparison to subjects not receiving the composition and may become infected. More preferably, clinical signs are reduced in subjects receiving the composition of the present invention by at least 20%, preferably by at least 30%, more preferably by at least 40%, and even more preferably by at least 50%.

Still further, the present invention is directed to a vaccine composition for the treatment or prevention of clinical signs caused by *Brachyspira hyodysenteriae* or a disease caused by *Brachyspira hyodysenteriae*; wherein said vaccine comprises the recombinant polypeptide of the invention or the immunogenic composition of the invention, and wherein the vaccine composition is also termed "the vaccine composition of the invention" herein.

In yet another preferred aspect, the immunogenic composition of the invention or the vaccine composition of the invention further contains one or more pharmaceutically acceptable carriers or excipients. Said one or more pharmaceutically acceptable carriers or excipients are preferably selected from the group consisting of solvents, dispersion media, adjuvants, stabilizing agents, diluents, preservatives, antibacterial and antifungal agents, isotonic agents, and adsorption delaying agents.

Also, the invention concerns the use of the recombinant polypeptide of the invention or of the immunogenic composition of the invention for the preparation of a medicament for generating an immune response to *Brachyspira hyodysenteriae* in an animal.

and, respectively, the invention also concerns the recombinant polypeptide of the invention or the immunogenic composition of the invention for use in a method for generating an immune response to *Brachyspira hyodysenteriae* in an animal.

Preferably, the generating of an immune response to *Brachyspira hyodysenteriae* in an animal, as described herein, results in the treatment or prevention of clinical signs caused by *Brachyspira hyodysenteriae* or of a disease caused by *Brachyspira hyodysenteriae* in said animal.

Another aspect of the invention concerns the use of a polynucleotide comprising a sequence which encodes the recombinant polypeptide of the invention for the preparation of a medicament for generating an immune response to *Brachyspira hyodysenteriae* in an animal.

Also, the invention concerns the use of two or three different polynucleotides, namely of (i) a polynucleotide comprising a sequence which encodes the recombinant polypeptide of the invention, and further (ii) a polynucleotide comprising a sequence which encodes a polypeptide that comprises or consists of a sequence that is at least 70%, preferably at least 80%, more preferably at least 90%, still more preferably at least 95% or in particular 100% identical to the sequence of SEQ ID NO: 3 and/or (iii) a polynucleotide comprising a sequence which encodes a polypeptide that comprises or consists of a sequence that is at least 70% identical to the sequence of SEQ ID NO: 5, for the preparation of a medicament for generating an immune response to *Brachyspira hyodysenteriae* in an animal, and, respectively, the invention also concerns said two or three different polynucleotides for use in a method for generating an immune response to *Brachyspira hyodysenteriae* in an animal.

Thus the invention in particular concerns the use of two different polynucleotides, namely of (i) a polynucleotide comprising a sequence which encodes the recombinant polypeptide of the invention and either (ii) a polynucleotide comprising a sequence which encodes a polypeptide that comprises or consists of a sequence that is at least 70%, preferably at least 80%, more preferably at least 90%, still more preferably at least 95% or in particular 100% identical to the sequence of SEQ ID NO: 3 or (iii) a polynucleotide comprising a sequence which encodes a polypeptide that comprises or consists of a sequence that is at least 70% identical to the sequence of SEQ ID NO: 5, for the preparation of a medicament for generating an immune response to *Brachyspira hyodysenteriae* in an animal, and, respectively, the invention also concerns said two different polynucleotides for use in a method for generating an immune response to *Brachyspira hyodysenteriae* in an animal.

Also, the invention in particular thus further concerns the use of three different polynucleotides, namely of (i) a polynucleotide comprising a sequence which encodes the recombinant polypeptide of the invention, and further (ii) a polynucleotide comprising a sequence which encodes a polypeptide that comprises or consists of a sequence that is at least 70%, preferably at least 80%, more preferably at least 90%, still more preferably at least 95% or in particular 100% identical to the sequence of SEQ ID NO: 3 and further (iii) a polynucleotide comprising a sequence which encodes a polypeptide that comprises or consists of a sequence that is at least 70% identical to the sequence of SEQ ID NO: 5, for the preparation of a medicament for generating an immune response to *Brachyspira hyodysenteriae* in an animal, and, respectively, the invention also concerns said three polynucleotides for use in a method for generating an immune response to *Brachyspira hyodysenteriae* in an animal.

As used herein, it is in particular understood that the term "identical to the sequence of SEQ ID NO: X" is equivalent to the term "identical to the sequence of SEQ ID NO: X over the length of SEQ ID NO: X" or to the term "identical to the sequence of SEQ ID NO: X over the whole length of SEQ ID NO: X", respectively. In this context, "X" is any integer selected from 1 to 6 so that "SEQ ID NO: X" represents any of the SEQ ID NOs mentioned herein.

Still another aspect of the invention concerns the use of a plasmid, preferably an expression vector, which comprises a polynucleotide comprising a sequence which encodes the recombinant polypeptide of the invention.

Also, the invention further concerns the use of two or three different plasmids, preferably expression vectors, namely of (i) a plasmid, preferably an expression vector, which comprises a polynucleotide comprising a sequence which encodes the recombinant polypeptide of the invention, and further (ii) a plasmid, preferably an expression vector, which comprises a polynucleotide comprising a sequence which encodes a polypeptide that is at least 70% preferably at least 80%, more preferably at least 90%, still more preferably at least 95% or in particular 100% identical to the sequence of SEQ ID NO: 3 and/or (iii) a plasmid, preferably an expression vector, which comprises a polynucleotide comprising a sequence which encodes a polypeptide that is at least 70%, preferably at least 80° A), more preferably at least 90%, still more preferably at least 95% or in particular 100% identical to the sequence of SEQ ID NO: 5, for the preparation of a medicament for generating an immune response to *Brachyspira hyodysenteriae* in an animal.

Thus, the invention particularly further concerns the use of two different plasmids, preferably expression vectors, namely of (i) a plasmid, preferably an expression vector, which comprises a polynucleotide comprising a sequence which encodes the recombinant polypeptide of the invention, and either (ii) a plasmid, preferably an expression vector, which comprises a polynucleotide comprising a sequence which encodes a polypeptide that is at least 70%, preferably at least 80%, more preferably at least 90%, still more preferably at least 95% or in particular 100% identical to the sequence of SEQ ID NO: 3 or (iii) a plasmid, preferably an expression vector, which comprises a polynucleotide comprising a sequence which encodes a polypeptide that is at least 70%, preferably at least 80%, more preferably at least 90%, still more preferably at least 95% or in particular 100% identical to the sequence of SEQ ID NO: 5, for the preparation of a medicament for generating an immune response to *Brachyspira hyodysenteriae* in an animal.

Also, the invention thus particularly further concerns the use of three different plasmids, preferably expression vectors, namely of (i) a plasmid, preferably an expression vector, which comprises a polynucleotide comprising a sequence which encodes the recombinant polypeptide of the invention and (ii) a plasmid, preferably an expression vector, which comprises a polynucleotide comprising a sequence which encodes a polypeptide that is at least 70%, preferably at least 80%, more preferably at least 90%, still more preferably at least 95% or in particular 100% identical to the sequence of SEQ ID NO: 3 and (iii) a plasmid, preferably an expression vector, which comprises a polynucleotide comprising a sequence which encodes a polypeptide that is at least 70%, preferably at least 80%, more preferably at least 90%, still more preferably at least 95% or in particular 100% identical to the sequence of SEQ ID NO: 5, for the preparation of a medicament for generating an immune response to *Brachyspira hyodysenteriae* in an animal.

Still a further aspect of the invention relates to the use of a cell comprising a plasmid, preferably an expression vector, which comprises a polynucleotide comprising a sequence which encodes the recombinant polypeptide of the invention.

Also, the invention relates to the use of two or three different cells, namely of (i) a cell comprising a plasmid, preferably an expression vector, which comprises a polynucleotide comprising a sequence which encodes the recombinant polypeptide of the invention, and further (ii) a cell comprising a plasmid, preferably an expression vector, which comprises a polynucleotide comprising a sequence which encodes a polypeptide that is at least 70%, preferably at least 80%, more preferably at least 90%, still more preferably at least 95% or in particular 100% identical to the sequence of SEQ ID NO: 3 and/or (iii) a cell comprising a plasmid, preferably an expression vector, which comprises a polynucleotide comprising a sequence which encodes a polypeptide that is at least 70%, preferably at least 80%, more preferably at least 90%, still more preferably at least 95% or in particular 100% identical to the sequence of SEQ ID NO: 5, for the preparation of a medicament for generating an immune response to *Brachyspira hyodysenteriae* in an animal.

Thus, the invention also relates to the use of two different cells, namely of (i) a cell comprising a plasmid, preferably an expression vector, which comprises a polynucleotide comprising a sequence which encodes the recombinant polypeptide of the invention, and either (ii) a cell comprising a plasmid, preferably an expression vector, which comprises a polynucleotide comprising a sequence which encodes a polypeptide that is at least 70%, preferably at least 80%, more preferably at least 90%, still more preferably at least 95% or in particular 100% identical to the sequence of SEQ ID NO: 3 or (iii) a cell comprising a plasmid, preferably an expression vector, which comprises a polynucleotide comprising a sequence which encodes a polypeptide that is at least 70%, preferably at least 80%, more preferably at least 90%, still more preferably at least 95% or in particular 100% identical to the sequence of SEQ ID NO: 5, for the preparation of a medicament for generating an immune response to *Brachyspira hyodysenteriae* in an animal.

Also, the invention thus relates to the use of three different cells, namely of (i) a cell comprising a plasmid, preferably an expression vector, which comprises a polynucleotide comprising a sequence which encodes the recombinant polypeptide of the invention and (ii) a cell comprising a plasmid, preferably an expression vector, which comprises a polynucleotide comprising a sequence which encodes a polypeptide that is at least 70%, preferably at least 80%, more preferably at least 90%, still more preferably at least 95% or in particular 100% identical to the sequence of SEQ ID NO: 3 and (iii) a cell comprising a plasmid, preferably an expression vector, which comprises a polynucleotide comprising a sequence which encodes a polypeptide that is at least 70%, preferably at least 80%, more preferably at least 90%, still more preferably at least 95% or in particular 100% identical to the sequence of SEQ ID NO: 5, for the preparation of a medicament for generating an immune response to *Brachyspira hyodysenteriae* in an animal.

According to yet a further aspect, the invention is also directed to the use of an expression vector comprising a polynucleotide which comprises the sequence of SEQ ID NO: 2 for the preparation of a medicament for treating or preventing a disease caused by *Brachyspira hyodysenteriae* in an animal in need of said treatment.

Also, the invention is directed to the use of two or three different expression vectors, namely of (i) an expression vector comprising a polynucleotide which comprises the sequence of SEQ ID NO: 2, and further (ii) an expression vector comprising a polynucleotide comprising the sequence of SEQ ID NO: 4 and/or (iii) an expression vector comprising a polynucleotide comprising the sequence of SEQ ID NO: 6, for the preparation of a medicament for treating or preventing a disease caused by *Brachyspira hyodysenteriae* in an animal in need of said treatment.

Thus, the invention is also directed to the use of two different expression vectors, namely of (i) an expression vector comprising a polynucleotide which comprises the sequence of SEQ ID NO: 2, and either (ii) an expression vector comprising a polynucleotide comprising the sequence of SEQ ID NO: 4 or (iii) an expression vector comprising a polynucleotide comprising the sequence of SEQ ID NO: 6, for the preparation of a medicament for treating or preventing a disease caused by *Brachyspira hyodysenteriae* in an animal in need of said treatment.

Also, the invention is thus directed to the use of three different expression vectors, namely of (i) an expression vector comprising a polynucleotide which comprises the sequence of SEQ ID NO: 2 and (ii) an expression vector comprising a polynucleotide comprising the sequence of SEQ ID NO: 4 and (iii) an expression vector comprising a polynucleotide comprising the sequence of SEQ ID NO: 6, for the preparation of a medicament for treating or preventing a disease caused by *Brachyspira hyodysenteriae* in an animal in need of said treatment.

According to another aspect, the invention further concerns the use of a cell containing an expression vector comprising a polynucleotide comprising the sequence of SEQ ID NO: 2 for the preparation of a medicament for treating or preventing a disease caused by *Brachyspira hyodysenteriae* in an animal in need of said treatment.

Also, the invention concerns the use of two or three different cells, namely of (i) a cell containing an expression vector comprising a polynucleotide comprising the sequence of SEQ ID NO: 2, and further (ii) a cell containing an expression vector comprising a polynucleotide comprising the sequence of SEQ ID NO: 4 and/or (iii) a cell containing an expression vector comprising a polynucleotide comprising the sequence of SEQ ID NO: 6, for the preparation of a medicament for treating or preventing a disease caused by *Brachyspira hyodysenteriae* in an animal in need of said treatment.

Thus, the invention also concerns the use of two different cells, namely of (i) a cell containing an expression vector comprising a polynucleotide comprising the sequence of SEQ ID NO: 2, and either (ii) a cell containing an expression vector comprising a polynucleotide comprising the sequence of SEQ ID NO: 4 or (iii) a cell containing an expression vector comprising a polynucleotide comprising the sequence of SEQ ID NO: 6, for the preparation of a medicament for treating or preventing a disease caused by *Brachyspira hyodysenteriae* in an animal in need of said treatment.

Also, the invention thus concerns the use of three different cells, namely of (i) a cell containing an expression vector comprising a polynucleotide comprising the sequence of SEQ ID NO: 2 and (ii) a cell containing an expression vector comprising a polynucleotide comprising the sequence of SEQ ID NO: 4 and (iii) a cell containing an expression vector comprising a polynucleotide comprising the sequence of SEQ ID NO: 6, for the preparation of a medicament for treating or preventing a disease caused by *Brachyspira hyodysenteriae* in an animal in need of said treatment.

According to still another aspect the invention is directed to the use of the recombinant polypeptide of the invention or of the immunogenic composition of the invention for the preparation of a medicament for treating or preventing a disease caused by *Brachyspira hyodysenteriae* in an animal in need of said treatment.

In yet a further aspect, the invention provides a method of generating an immune response to *Brachyspira hyodysenteriae* in an animal comprising administering to said animal the polypeptide of the invention or the immunogenic composition of the invention.

Hence the invention provides a method of generating an immune response to *Brachyspira hyodysenteriae* in an animal, wherein said method comprises the step of administering to said animal the recombinant polypeptide of the invention or the immunogenic composition of the invention. Preferably, a therapeutically effective amount of the recombinant polypeptide of the invention is administered, wherein in particular 5 μg to 5 mg, preferably 50 μg to 2 mg, or more preferably 100 μg to 1 mg, or most preferably 250 μg to 750 μg of the recombinant protein of the invention are understood to be a therapeutically effective amount of the recombinant protein of the invention.

Thus, the invention also relates to the recombinant polypeptide of the invention or the immunogenic composition of the invention for use in a method of generating an immune response to *Brachyspira hyodysenteriae* in an animal, wherein in said method preferably a therapeutically effective amount of the recombinant polypeptide of the invention or of the recombinant polypeptide(s) contained in the immunogenic composition of the invention is to be administered.

In still a further aspect, the invention also provides a method of treating or preventing a disease caused by *Brachyspira hyodysenteriae* in an animal in need of said treatment comprising administering to said animal a therapeutically effective amount of the vaccine composition of the invention.

Examples

1.0. Partial Genome Sequencing of *Brachyspira hyodysenteriae* (Strain WA1)

1.1. Materials and Methods 1.1.1. Genome sequencing

An Australian porcine field isolate of *B. hyodysenteriae* (strain WA1) is shotgun sequenced. This strain has been well-characterised and shown to be virulent following experimental challenge of pigs. The spirochaete is grown in anaerobic trypticase soy broth culture and high molecular weight genomic DNA suitable for preparation of genomic DNA libraries was purified using a cesium chloride gradient following a standard cetyltrimethylammonium bromide (CTAB) extraction method. The genomic DNA is mechanically sheared and the fragmented DNA is cloned into the pSMART vector system. A small insert (2-3 kb) library and a medium insert (3-10 kb) library are constructed into the low copy version of the pSMART vector. Sequencing of the whole genome is undertaken using a Sanger/pyrosequencing hybrid approach. The first round of sequencing is performed via Sanger sequencing of the pSMART libraries. The second round of high-throughput sequencing is performed using pyrosequencing approach on a Roche-454 GS20 instrument. Finally, remaining gaps in the genome sequence are closed by PCR walking between un-linked contiguous sequences to finish the genome sequence.

1.1.2. Annotation

All genome sequences for *B. hyodysenteriae* are assembled and annotated by the Australian Genome Research Facility (AGRF) in Queensland and at Murdoch University by the Centre for Comparative Genomics (CCG). A range of public domain bioinformatics tools are used to analyse and re-analyse the sequences as part of a quality assurance procedure on data analysis. Open reading frames (ORFs) are predicted using a variety of programs including GeneMark, GLIMMER, ORPHEUS, SELFID and GetORF. Putative ORFs are examined for homology (DNA and protein) with existing international databases using searches including BLAST and FASTA. Phylogenetic and other molecular evolution analysis is conducted with the identified genes and with other species to assist in the assignment of function. The in silico analysis of the partially sequenced genome produces a comprehensive list of all the predicted ORFs present in the sequence data available.

1.1.3. Analysis of Gene Distribution Using Polymerase Chain Reaction (PCR)

Two primer pairs which anneal to different regions of the target gene coding region are designed and optimised for PCR detection. Distribution analysis of the *B. hyodysenteriae* target genes are performed on 23 strains of *B. hyodysenteriae*, including two strains which have been shown to be a virulent. Primer sets used in the distribution analysis are shown in Table 1. PCR analysis is performed in a 25 μl total volume using Taq DNA polymerase. The amplification mixture consists of 1×PCR buffer (containing 1.5 mM of $MgCl_2$), 1 U of Taq DNA polymerase, 0.2 mM of each dNTP, 0.5 μM of the primer pair, and 1 μl purified chromosomal template DNA. Cycling conditions involves an initial template denaturation step of 5 min at 94° C., followed by 30 cycles of denaturation at 94° C. for 30 s, annealing at 50° C. for 15 s, and primer extension at 72° C. for 1 min. The PCR products are subjected to electrophoresis in 1% (w/v) agarose gels in 1×TAE buffer (40 mM Tris-acetate, 1 mM EDTA), staining with a 1 μg/ml ethidium bromide solution and viewing over ultraviolet (UV) light.

1.2. Results and Discussion 1.2.1. Bioinformatics

Sequencing of the *B. hyodysenteriae* WA1 genome results in the identification of a 3,000,694 bp genome and a 35,940 bp circular extra-chromosomal plasmid. The genome is predicted to encode 2,551 ORFs and the plasmid encodes 32 ORFs. Comparison of the predicted ORFs with genes present in the nucleic acid and protein databases indicates that approximately 70% of the predicted ORFs with putative function. The remaining 30% of the ORFs have no known function.

1.2.2. Vaccine Candidates

ORFs showing strong similarity with bacterial outer surface proteins present in the public databases are selected as potential vaccine targets. Table 2 shows the genes selected as potential vaccine targets and their putative function.

1.2.3. Gene Distribution

The overall gene distribution of each ORF is summarized in Table 3. The distribution is determined from the cumulative result of PCR using up to two different primer sets. All of the ORFs are present in 100% of the *B. hyodysenteriae* strains tested.

2.0. Cloning, Expression and Purification of Vaccine Components 2.1. Materials and Methods 2.1.1. Plasmid Extraction

*Escherichia coli* JM109 clones harbouring the pTrcHis plasmid (Invitrogen) are streaked out from glycerol stock storage onto Luria-Bertani (LB) agar plates supplemented with 100 mg/l ampicillin and incubated at 37° C. for 16 h. A single colony is used to inoculate 10 ml of LB broth supplemented with 100 mg/l ampicillin and the broth culture is incubated at 37° C. for 12 h with shaking. The entire overnight culture is centrifuged at 5,000×g for 10 min and the plasmid contained in the cells extracted using the QIAprep Spin Miniprep Kit (Qiagen). The purified plasmid is quantified using the NanoDrop ND-1000 spectrophotometer and the DNA concentration adjusted to 100 μg/ml by dilution with TE (10 mM Tris-HCl, 1 mM EDTA, pH 8.0) buffer. The purified pTrcHis plasmid is stored at −20° C.

2.1.2. Vector Preparation

Two μg of the purified pTrcHis plasmid is digested at 37° C. for 1-4 h in a total volume of 50 μl containing 100 mM Tris-HCl (pH 7.5), 50 mM NaCl, 10 mM $MgCl_2$, 1 mM DTT, 100 μg/ml bovine serum albumin (BSA) and 5 U of Xhol and EcoRl. The linearised pTrcHis vector is purified using the UltraClean PCR Clean-up Kit (Mo Bio Laboratories). The purified linear vector is quantified using the NanoDrop ND-1000 spectrophotometer and the DNA concentration adjusted to 50 μg/ml by dilution with TE buffer. The linearised vector is stored at −20° C.

2.1.3. Insert Preparation 2.1.3.1. Primer Design

Primer pairs are designed to amplify as much of the coding region of the target gene as possible. All primers sequences include terminal restriction enzyme recognition sites to enable cohesive-end ligation of the resultant amplicon into the linearised pTrcHis vector. The primer sequences used for cloning are shown in Table 5. The translation of the chimeric pTrcHis expression cassette is deduced using Vector NTI Advance version 10 (Invitrogen) to confirm that the gene inserts will be expressed in the correct reading frame.

2.1.3.2. Amplification of the Gene Inserts

All target gene inserts are amplified by PCR in a 100 μl total volume using Taq DNA polymerase and Pfu DNA polymerase. The amplification mixture consists of 1×PCR buffer (containing 1.5 mM of $MgCl_2$), 1 U of Taq DNA polymerase, 0.01 U Pfu DNA polymerase, 0.2 mM of each dNTP, 0.5 μM of the appropriate primer pair and 1 μl of purified chromosomal DNA. The chromosomal DNA is prepared from the same *B. hyodysenteriae* strain used for genome sequencing. Cycling conditions involves an initial template denaturation step of 5 min at 94° C., followed by 30 cycles of denaturation at 94° C. for 30 s, annealing at 50° C. for 15 s, and primer extension at 72° C. for 1 min. The PCR products are subjected to electrophoresis in 1% (w/v) agarose gels in 1×TAE buffer, staining with a 1 μg/ml ethidium bromide solution and viewing over UV light. After verifying the presence of the correct size PCR product, the PCR reaction is purified using the UltraClean PCR Clean-up Kit (Mo Bio Laboratories).

2.1.3.3. Restriction Enzyme Digestion of the Gene Inserts

Thirty μl of the purified PCR product is digested in a 50 μl total volume with 1 U of Xhol and 1 U of EcoRl. The digested insert DNA is purified using the UltraClean PCR Clean-up Kit (Mo Bio Laboratories). Purified digested insert DNA is quantified using the NanoDrop ND-1000 spectrophotometer and the DNA concentration adjusted to 20 μg/ml by diluting with TE buffer. The purified restricted insert DNA are used immediately for vector ligation.

2.1.4. Ligation of the Gene Inserts into the pTrcHis Vector

Ligation reactions are all performed in a total volume of 20 μl. One hundred ng of linearised pTrcHis is incubated with 20 ng of restricted insert at 16° C. for 16 h in 30 mM Tris-HCl (pH 7.8), 10 mM $MgCl_2$, 10 mM DTT and 1 mM ATP containing 1 U of T4 DNA ligase. An identical ligation reaction containing no insert DNA is also included as a vector re-circularisation negative control.

2.1.5. Transformation of pTrcHis Ligations into *E. coli* Cells

Competent *E. coli* JM109 cells are thawed from −80° C. storage on ice and 50 μl of the cells are transferred into ice-cold 1.5 ml microfuge tubes containing 5 μl of the overnight ligation reactions. The tubes are mixed by gently tapping the bottom of each tube on the bench and left on ice for 30 min. The cells are then heat-shocked by placing the tubes into a 42° C. waterbath for 45 s before returning the tube to ice for 2 min. The transformed cells are recovered in 1 ml LB broth for 1 h at 37° C. with gentle mixing. The recovered cells are harvested at 2,500×g for 5 min and the cells resuspended in 50 μl of fresh LB broth. The entire 50 μl of resuspended cells is spread evenly onto a LB agar plate containing 100 mg/l ampicillin using a sterile glass rod. Plates are incubated at 37° C. for 16 h.

2.1.6. Detection of Recombinant pTrcHis Constructs in *E. coli* by PCR

Twelve single transformant colonies for each construct are streaked onto fresh LB agar plates containing 100 mg/l ampicillin and incubated at 37° C. for 16 h. A single colony from each transformation event is resuspended in 50 μl of TE buffer and boiled for 1 min. Two μl of boiled cells are used as template for PCR. The amplification mixture consists of 1×PCR buffer (containing 1.5 mM of $MgCl_2$), 1 U of Taq DNA polymerase, 0.2 mM of each dNTP, 0.5 μM of the pTrcHis-F primer (5'-CAATTTATCAGACAATCTGT-GTG-3')(SEQ ID NO:19) and 0.5 μM of the pTrcHis-R primer (5'-TGCCTGGCAGTTCCCTACTCTCG-3') (SEQ ID NO:20). Cycling conditions involves an initial template denaturation step of 5 min at 94° C., followed by 30 cycles of denaturation at 94° C. for 30 s, annealing at 60° C. for 15 s, and a primer extension at 72° C. for 1 min. The PCR products are subjected to electrophoresis in 1% (w/v) agarose gels in 1×TAE buffer, staining with a 1 μg/ml ethidium bromide solution and viewing over UV light.

2.1.7. Pilot Expression of Recombinant his-Tagged Proteins

Three isolated *E. coli* JM109 colonies harbouring the recombinant constructs are inoculated into 3 ml LB broth in a 5 ml tube containing 100 mg/l ampicillin and 1 mM IPTG and incubated at 37° C. for 16 h with shaking. The cells are harvested by centrifugation at 5,000×g for 10 min at 4° C. The supernatant is discarded and each pellet is resuspended with 1 ml Ni-NTA denaturing lysis buffer (100 mM $NaH_2PO_4$, 10 mM Tris-HCl, 6 M GuCl, pH 8.0). After vortexing the tube for 1 min, the cellular debris is pelleted by centrifugation at 10,000×g for 10 min at 4° C. The supernatant is transferred to a new tube and stored at −20° C. until analysis.

2.1.8. Sodium Dodecyl Sulfate Polyacrylamide Gel Electrophoresis (SDS-PAGE)

SDS-PAGE analysis of protein involves electrophoretic separation using a discontinuous Tris-glycine buffer system. Thirty μl of protein sample is mixed with 10 μl of 4× sample treatment buffer (250 mM Tris-HCl pH 6.0, 8% w/v SDS, 200 mM DTT, 40% v/v glycerol and 0.04% w/v bromophenol blue). Samples are boiled for 5 min immediately prior to loading 10 μl of the sample into wells in the gel. The gel comprises a stacking gel (125 mM Tris-HCl ph 6.8, 4% w/v acylamide, 0.15% w/v bis-acrylamide and 0.1% w/v SDS) and a separating gel (375 mM Tris-HCl ph 8.8, 12% w/v acylamide, 0.31% w/v bis-acrylamide and 0.1% w/v SDS). These gels are polymerised by the addition of 0.1% (v/v) TEMED and 0.05% (w/v) freshly prepared ammonium sulphate solution and cast into the mini-Protean dual slab cell (Bio-Rad). Samples are run at 150 V at room temperature (RT) until the bromophenol blue dye-front reaches the bottom of the gel. Pre-stained molecular weight standards are electrophoresed in parallel with the samples in order to allow molecular weight estimations. After electrophoresis, the gel is immediately stained using Coomassie Brilliant Blue G250 or subjected to electro-transfer onto nitrocellulose membrane for Western blotting.

2.1.9. Western Blot Analysis

Electrophoretic transfer of separated proteins from the SDS-PAGE gel to nitrocellulose membrane is performed using the Towbin transfer buffer system. After electrophoresis, the gel is equilibrated in transfer buffer (25 mM Tris, 192 mM glycine, 20% v/v methanol, pH 8.3) for 15 min. The proteins in the gel are transferred to nitrocellulose membrane using the mini-Protean transblot apparatus (Bio-Rad). The nitrocellulose membrane containing the separated proteins is blocked with 10 ml of tris-buffered saline (TBS; 20 mM Tris-HCl, 500 mM NaCl, pH 7.5) containing 5% (w/v) skim milk powder for 1 h at RT. The membrane is washed with TBS containing 0.1% (v/v) Tween 20 (TBST) and then incubated with 10 ml mouse anti-his antibody (diluted 5,000-fold with TBST) for 1 h at RT. After washing three times for 5 min with TBST, the membrane is incubated with 10 mL goat anti-mouse IgG (whole molecule)-AP diluted 5,000-fold in TBST for 1 h at RT. The membrane is developed for visualisation using the Alkaline Phosphatase Substrate Kit (Bio-Rad).

2.1.10. Verification of Reading Frame of the Recombinant pTrcHis Constructs by Direct Sequence Analysis

*E. coli* clones for each construct are inoculated into 10 ml LB broth containing 100 mg/l ampicillin and incubated at 37° C. for 12 h with shaking. The entire overnight culture is centrifuged at 5,000×g for 10 min and the plasmid contained in the cells extracted using the QIAprep Spin Miniprep Kit. The purified plasmid is quantified using the NanoDrop ND-1000 spectrophotometer. The plasmids are subjected to automated direct sequencing of the pTrcHis expression cassette using the pTrcHis-F and pTrcHis-R primers. Each sequencing reaction is performed in a 10 μl volume consisting of 200 ng of plasmid DNA, 2 pmol of primer, 4 μl of the ABI PRISM™ BigDye Terminator Cycle Sequencing Ready Reaction Mix (PE Applied Biosystems) and 1 μl of 5× dilution buffer. Cycling conditions involve a 2 min denaturing step at 96° C., followed by 25 cycles of denaturation at 96° C. for 10 s and a combined primer annealing and extension step at 60° C. for 4 min. Residual dye terminators are removed from the sequencing products by precipitation with 95% (v/v) ethanol containing 85 mM sodium acetate (pH 5.2), 3 mM EDTA (pH 8), and vacuum dried. The plasmids are sequenced in duplicate using each primer. Sequencing products are analysed using an ABI 373A DNA Sequencer (PE Applied Biosystems).

2.1.11. Serology Using Purified Recombinant Protein

Ten μg of purified recombinant protein is diluted in 10 ml of carbonate buffer and 100 μl is added to each well of a 96-well microtitre plate. The protein is allowed to coat overnight at 4° C. The plate is blocked with 150 μl of PBS-BSA (1% w/v) in each well for 1 hour at room temperature (RT) with mixing and then washed three times with 150 μl of PBST (0.05% v/v). Pig sera are diluted 1:800 in 100 μl of PBST-BSA (0.1% w/v) and incubated at RT for 2 hours with mixing. Plates are washed before adding 100 μl of goat anti-swine IgG (whole molecule)-HRP diluted 1:5, 000 in PBST. After incubating for 1 hr at RT, the plates are washed and 100 μl of TMB substrate added. Colour development is allowed to occur for 10 minutes at RT before being stopped with the addition of 50 μl of 1 M sulphuric acid. The optical density of each well is read at 450 nm. Pooled serum from pigs of different sources and health status are used in this analysis. These included pigs from high health status herds (N1-N3), hyperimmunized pigs (M1-M3), experimentally challenged pigs (H1-H5) and recovered pigs from different herds (H6-H13).

2.2. Results and Discussion 2.2.1. Construction of the Recombinant pTrcHis Constructs Cloning of the various inserts into the pTrcHis expression vector produces recombinant constructs of various sizes. Nucleotide sequencing of the pTrcHis constructs verifies that the expression cassette is in the correct frame for all the constructs. The predicted translation of the pTrcHis expression cassette indicates that all the recombinant his-tagged proteins and the deduced amino acid sequence of the native spirochaete proteins are identical.

2.2.2. Expression and Purification of Recombinant Proteins

Expression of the selected recombinant *E. coli* clones is initially performed in preparative-scale. All cloned genes produces recombinant proteins possessing the hexa-histidine fusion (4 kDa) with an apparent molecular weight similar to the predicted molecular weight of the native protein (Table 4). The recombinant proteins are highly reactive in western blotting using the anti-his antibody. Purification of the his-tagged recombinant proteins by affinity chromatography under denaturing conditions is successful. SDS-PAGE and Coomassie Blue staining of all recombinant proteins showed that a purification of at least 70% is achieved.

2.2.3. Serology

All proteins react strongly with serum from the pig hyperimmunized with *B. hyodysenteriae* bacterin (M1; 1.5881±0.0662) and re acts less strongly with serum from pigs hyperimmunized with *B. pilosicoli* (M2; 1.0966±0.0358) and *B. innocens* (M3; 1.0920±0.0290) indicating some level of cross-reactivity with pigs recognising other *Brachyspira* spp. The proteins react weakest with serum taken from high-health status pigs (N1-N3; 0.2049 to 0.4485), followed by experimentally challenged pigs showing acute severe symptoms of SD (H1-H5; 0.5456 to 0.9922), and strongest with pigs which have recovered from SD (H6-H13; 0.8075 to 1.3425). As a whole, these results indicate that all these putative surface proteins are immunogenic in naturally and experimentally infected pigs.

3.0. Expression and Purification of Proteins for Vaccine Formulation 3.1. Materials and Methods 3.1.1. Expression and Purification of Recombinant his-Tapped Proteins A single colony of the recombinant pTrcHis construct in *E. coli* JM109 is inoculated into 50 ml LB broth in a 250 ml conical flask containing 100 mg/l ampicillin and incubated at 37° C. for 16 h with shaking. A 5 l conical flask containing 1 l of LB broth supplemented with 100 mg/l ampicillin is inoculated with 25 ml of the overnight culture and incubated at 37° C. until the optical density of the cells at 600 nm is 0.5. The culture is then induced by adding IPTG to a final concentration of 1 mM and the cells returned to 37° C. with shaking. After 5 h of induction, the culture is transferred to 250 ml centrifuge bottles and the bottles are centrifuged at 3,000×g for 20 min at 4° C. The supernatant is discarded and each pellet is resuspended with 8 ml Ni-NTA denaturing lysis buffer (100 mM $NaH_2PO_4$, 10 mM Tris-HCl, 6 M GuCl, pH 8.0). The resuspended cells are stored at −20° C. overnight.

The cell suspension is removed from −20° C. storage and thawed on ice. The cell lysate is then sonicated on ice 3 times for 30 s with 1 min incubation on ice between sonication rounds. The lysed cells are cleared by centrifugation at 20,000×g for 10 min at 4° C. and the supernatant is transferred to a 15 ml column containing a 0.5 ml bed volume of Ni-NTA agarose resin (Qiagen). The recombinant his-tagged protein is allowed to bind to the resin for 1 h at 4° C. with end-over-end mixing. The resin is then washed with 30 ml of Ni-NTA denaturing wash buffer (100 mM $NaH_2PO_4$, 10 mM Tris-HCl, 8 M urea, 20 mM imidazole, pH 8.0) before elution with 15 ml of Ni-NTA denaturing elution buffer (100 mM $NaH_2PO_4$, 10 mM Tris-HCl, 8 M urea, 250 mM imidazole, pH 8.0). Three 5 ml fractions of the eluate are collected and stored at 4° C. Thirty μl of each eluate is treated with 10 μl of 4× sample treatment buffer and boiled for 5 min. The samples are subjected to SDS-PAGE and stained with Coomassie Brilliant Blue G250.

3.1.2. Re-Folding and Lyophilisation of the Purified Recombinant his-Tagged Protein The eluted proteins are pooled and transferred into a hydrated dialysis tube with a molecular weight cut-off (MWCO) of 3,500 Da. A 200 μl aliquot of the pooled eluate is taken for quantification using a commercial Protein Assay (Bio-Rad). The proteins are re-folded using the Novagen Protein Re-folding Kit. The re-folded proteins are transferred from the dialysis tube into a 50 ml centrifuge tubes (40 ml maximum volume) and the tubes are placed at −80° C. overnight. Tubes are placed into a freeze-drier and lyophilised to dryness. The lyophilised proteins are then re-hydrated with PBS to a concentration of 2 mg/ml and stored at −20° C.

3.2. Results and Discussion 3.2.1. Expression and Purification of Recombinant Proteins Expression of the recombinant *E. coli* clones in medium-scale to generate sufficient recombinant protein for vaccine formulation is successful. Purification of the recombinant proteins by affinity chromatography under denaturing conditions yields a purity of at least 70%. Recombinant protein yields of 1 mg/l are consistently obtained using this expression protocol.

4.0. Protection Studies in Pigs

In the protection studies three vaccine formulations containing pairs of the three recombinant proteins (OMP6 protein, OMP7 protein and OMP10 protein) were tested, amongst others, and are described hereinafter in detail.

4.1. Materials and Methods 4.1.1. Pigs and Housing

Each test group included 11 castrated male pigs (Large White×Landrace×Duroc) of approximately 5-5.5 weeks of age purchased from a commercial piggery that is known to be free of swine dysentery, based on clinical history and microbiological testing.

4.1.2. Vaccine Preparations

The three recombinant proteins are expressed, purified and quantified under medium-scale conditions. Each vaccine consisted of an emulsion comprising of 20% (v/v) EMULSIGEN® (water-in-oil adjuvant) and 80% (v/v) recombinant protein resuspended in phosphate buffered saline (SOP: VACCPREP001:01). Two ml of vaccine contained 500 μg of each of the recombinant proteins for the treatment group as listed in Table 4.

4.1.3. Bleeding and Vaccination

When the pigs were approximately 6-6.5 weeks of age, rectal swabs were taken for *Brachyspira* culture and the pigs were weighed, individually bled from the anterior vena cava using a vacutainer and a 20-gauge needle, and then were vaccinated intramuscularly in the neck with 2 ml of the appropriate vaccine. The control pigs received adjuvant in PBS. Three weeks later the pigs were bled again, and received a second intramuscular vaccination in the neck. They were then transferred to a stage 2 experimental diet made in mash form.

4.1.4. Experimental Infection

Two weeks after the second vaccination the pigs were weighed, bled, and experimentally challenged with a mixture of strains of *B. hyodysenteriae*. Briefly, a gastric tube was used to dose each pig, such that each animal received a slurry of 100 ml of mixtures of mid log-phase broth culture (~10° cells/ml) containing five strains of *B. hyodysenteriae* together with chopped agar from a blood agar plate with a dense spirochaete growth on it. This procedure was repeated daily on the following two days. On the following two days the food for the pigs was inoculated with more of the spirochaetes, such that each pig would receive ~2 blood agar plates with a dense spirochaete growth 4.1.5. Health Monitoring The pigs were observed daily for signs of ill-health. Starting three days after the end of the experimental infection, rectal swabs were taken from each pig twice weekly and cultured for *B. hyodysenteriae*. When diarrhoea containing fresh blood and mucus was observed the pigs were recorded as having swine dysentery, and they were removed for post-mortem examination within 48 h, depending on the availability of the post-mortem facilities. Some other pigs that developed chronic diarrhoea without blood and mucus and that lost body condition also were removed on welfare grounds. The remaining pigs that did not develop clinical signs were killed five weeks after the start of the experimental infection 4.1.6. Post-Mortem Examination The pigs were stunned using a captive bolt pistol and then exsanguinated by severing the carotid artery. Blood was collected for serology. The carcass was opened and the intestinal tract removed. The large intestine was opened along its length and intestinal contents were collected from the caecum and proximal colon for spirochaete culture. Portions of the colonic wall at the same sites were placed in 10% buffered formalin for later histological examination. Observations of gross pathological changes and their distribution in the large intestine were recorded.

4.1.7. Spirochaete Culture

Samples were cultured for *Brachyspira* species and any positive growth was subjected to PCR amplification for *B. hyodysenteriae*.

4.1.8. ELISA Assays

Serum antibody levels against the individual recombinant proteins in each vaccine are measured using an indirect ELISA approach. Antibody levels in the serum of the control group and the vaccinated groups against recombinant Bpmp72, an outer envelope protein of *Brachyspira* pilosicoli, and against whole cell preparations of each of the five strains of *B. hyodysenteriae* used for infection, and the combination of the five strains, also were measured in ELISA.

4.2. Results 4.2.1. Antibody Levels

The serum antibody levels for the test groups with respect to time and vaccination showed antibody levels against the three recombinant proteins, respectively. For each of the three ELISA antigens, pigs vaccinated with the corresponding protein showed good secondary increases in antibody levels against that antigen, although the primary responses were low. The unvaccinated control pigs showed only minor time related increases in antibody levels. There were some increases in antibody levels in the pigs that were not vaccinated with the corresponding antigen, presumably due to cross reactivity between antigens, most noticeable with the OMP10 ELISA antigen in pigs vaccinated with the combination containing OMP6+OMP7.

At post-mortem, following the experimental infection, mean antibody levels against these proteins were not further elevated, and in most cases were reduced, and sometimes substantially. The standard deviations of the values were similar pre-infection and post-infection.

Antibody levels in the test groups of pigs against unrelated recombinant surface protein Bpmp72 of *B. pilosicoli* were uniformly low and generally did not increase with time.

Serum antibody levels of the pigs in the test groups against five individual whole cell preparation of *B. hyodysenteriae* representing the challenge strains, and a mixture of all five strains, for all individual preparations and for the combination, antibody levels only increased marginally pre-infection in all the groups of pigs, and then increased substantially post-infection.

Regarding the relative increase for each of the treatment groups to each of the whole cell antigen preparations with time, small increases were observed post-vaccination against all preparations, but again were most prominent post-infection. Antibody levels to the preparation made from strain BW1 was greatest in each ELISA post-infection, but the difference was not marked, and antibody levels against all strains increased.

4.2.2. Fecal Excretion of Spirochaetes

*Brachyspira* species were not found in the faeces of the pigs at purchase or prior to infection. The pattern of fecal excretion of *B. hyodysenteriae* with time by individual pigs following infection is shown in Table 6. All pigs excreted large numbers of spirochaetes at multiple sampling times before the end of the experiment at day 31.

4.2.3. Clinical Signs

Pigs having dysentery, or chronic diarrhoea and weight loss that necessitated killing them on welfare grounds, were removed before the end of the experiment (day 31) for post-mortem (Table 7). The greatest number of pigs was removed 10 days after the start of the experimental infection, emphasizing the severity of the challenge.

The fewest pigs removed before the end of the experiment were from the (OMP7+OMP10) group (2 pigs), and the most that were removed were from the control group (10 pigs). The other two groups had eight pigs (OMP6+OMP7) and seven pigs (OMP6+OMP10) removed due to disease.

At the end of the experiment, on day 31 after the start of infection, all remaining pigs were recorded as having either dysentery or diarrhoea at post-mortem.

4.3 Post-Mortem Findings

A summary of the post-mortem findings at the pig level is presented in Table 8, and a summary of results at the group level is presented in Table 9. All but one pig (group 2) had some lesions in the large intestine at slaughter (Table 10). All 11 of the control pigs had moderate to severe or severe lesions in the large intestine at slaughter. Group 2 had the most pigs with only mild lesions (4 pigs) and the fewest with severe lesions (3 pigs). When comparing combined normal/mild/moderate lesions to moderate/moderately sever/sever lesions, group 2 had the greatest number of pigs with less severe lesions, and also had the least pigs with the severe lesions (Table 11).

The caecums and colons of all pigs were heavily colonised with spirochaetes at post-mortem.

DISCUSSION AND CONCLUSIONS

In this experiment 10/11 control pigs (91%) developed clinical signs of swine dysentery before the end of the experiment, and all 11 had severe lesions in the large intestine at post-mortem. These results indicate that the method used to induce disease was highly effective. Antibody levels were elevated against whole cell preparations of all five infecting strains, suggesting that all proliferated in these pigs. However, as antibody levels against strain BW1 were the highest, it may be that this strain proliferated the most.

The serological responses to vaccination were consistent across the groups. The response to the first vaccination was relatively weak in all cases, although the secondary response was robust. A striking subsequent feature was the reduction in antibody levels to the specific antigens in nearly all cases following infection (at post-mortem). Antibody levels against these proteins did not go down in the pigs that were not vaccinated with them (even though they had some [relatively low] levels of cross-reacting antibodies), and antibody levels to whole cell preparations went up in all groups post-infection. It is possible that serum antibody against the vaccine components was being exported to and consumed in the colon of these pigs, all of which were heavily colonised. However, the antigen-specific nature of this decline in antibody levels does suggest the possibility of some form of antigen-specific tolerance being generated perhaps associated with the high antigen (protein) concentration used in these vaccines. The protein concentrations used may be very close to some level above which tolerance is generated.

Of the vaccinated groups, group 2 showed the best level of protection against development of colonic lesions, and group 2 had the fewest number of pigs removed before the end of the experiment.

Altogether, the results show that protection may be conferred by OMP10.

TABLE 1

Oligonucleotide primers used in the PCR distribution analysis of the *B. hyodysenteriae* vaccine candidate genes.

| Gene | Primer name | Primer Sequence (5'-3') |
|---|---|---|
| OMP6 | OMP6-F130 | GAACCAAAACCAGAAGAAGTAG (SEQ ID NO: 7) |
| | OMP6-R432 | TTTAGCCCTTACAACAGAAAG (SEQ ID NO: 8) |
| OMP7 | OMP7-F14 | TTTTACTTATGTCAGTAGTTATTATAGCAG (SEQ ID NO: 9) |
| | OMP7-R575 | AAATCGTTATACTTTTTCAAATCATC (SEQ ID NO: 10) |
| OMP10 | OMP10-F118 | TTCAGAAATAGTAAAAATCAGAGAG (SEQ ID NO: 11) |
| | OMP10-R646 | TTGGGAATCTTGCTGC (SEQ ID NO: 12) |

TABLE 2

Putative function of the *B. hyodysenteriae* genes based on similarity with the amino acid sequence of similar bacterial proteins obtained from the SWISS-PROT database.

| Gene | Putative function | E-value |
|---|---|---|
| OMP6 | OmpA family protein | 4e–115 |
| OMP7 | peptidoglycan-associated outer membrane lipoprotein | 1e–144 |
| OMP10 | OmpA family protein | 4e–159 |

TABLE 3

Gene distribution of the *B. hyodysenteriae* vaccine candidates. The gene distribution was analysed by PCR using a panel of 23 different strains.

| Gene | Distribution (%) |
|---|---|
| OMP6 | 100 |
| OMP7 | 100 |
| OMP10 | 100 |

TABLE 4

Recombinant protein components used in the seven vaccines. Each group consisted of 11 pigs. The negative control group received adjuvant alone. The identity of the proteins is shown in the lower panel.

| Group | Vaccine antigen |
|---|---|
| 1 | OMP6, OMP7 |
| 2 | OMP7, OMP10 |
| 3 | OMP6, OMP10 |
| 4 | Negative control |

TABLE 5

Oligonucleotide primers used in the cloning of the *B. hyodysenteriae* genes into the pTrcHis *E. coli* expression vector. The apparent molecular weight was determined from SDS-PAGE.

| Gene | Primer name | Primer Sequence (5'-3') | Predicted MW of native protein (kDa) | Apparent MW of recombinant protein (kDa) |
|---|---|---|---|---|
| OMP6 | OMP6-F22-Xho1 | TTACTCGAGTTTAGTTTATTGATCTTTGTCATAG (SEQ ID NO: 13) | 23.9 | 24.3 |
| | OMP-R640-EcoR1 | ACTGAATTCAGTTTCCCTGATATGTACTTTC (SEQ ID NO: 14) | | |
| OMP7 | OMP7-F16-Xho1 | AAACTCGAGTTACTTATGTCAGTAGTTATTATAGCAG (SEQ ID NO: 15) | 22.6 | 28.2 |
| | OMP7-R581-EcoR1 | TCGGAATTCTTGGCAAAATCGTTATACTTT (SEQ ID NO: 16) | | |
| OMP10 | OMP10O-F22-Xho1 | TTACTCGAGTTAATAATAACTTGCTTTATGAGTTC (SEQ ID NO: 17) | 25.2 | 31.1 |
| | OMP10-R650-EcoR1 | CTAGATTCGGTATTGGGAATCTTGCTG (SEQ ID NO: 18) | | |

TABLE 6

Scores for faecal shedding of *Brachyspira hyodysenteriae* on the days of sampling

| Pig no. | Group | Pre-infection | Days after the first day of experimental infection 7 | 10 | 14 | 17 | 21 | 24 | 28 |
|---|---|---|---|---|---|---|---|---|---|
| 16 | 1 | 0 | 0 | 5 | 5 | 5 | Dead | | |
| 24 | 1 | 0 | 5 | 5 | 5 | 5 | 5 | Dead | |
| 28 | 1 | 0 | 5 | Dead | | | | | |
| 31 | 1 | 0 | 5 | 5 | 5 | 5 | 5 | Dead | |
| 34 | 1 | 0 | 5 | 5 | 5 | 5 | 5 | | |
| 37* | 1 | 0 | 5 | 5 | 5 | 5 | 5 | Dead | |
| 60 | 1 | 0 | 5 | 5 | 5 | 5 | 5 | 5 | 5 |
| 61 | 1 | 0 | 5 | Dead | | | | | |
| 75 | 1 | 0 | 1 | 5 | 5 | 5 | 5 | 5 | 5 |
| 76 | 1 | 0 | 1 | 3 | 5 | 5 | 5 | 5 | 5 |
| 82 | 1 | 0 | 4 | 5 | 5 | 5 | 5 | 5 | 5 |
| 1 | 2 | 0 | 5 | 5 | 5 | 5 | 5 | 5 | 5 |
| 7 | 2 | 0 | 0 | 0 | 5 | 5 | 5 | 5 | 5 |
| 27 | 2 | 0 | 3 | 5 | 5 | 5 | 5 | 5 | 5 |
| 40 | 2 | 0 | 5 | 5 | 5 | 5 | 5 | Dead | |
| 42 | 2 | 0 | 5 | Dead | | | | | |
| 45 | 2 | 0 | 3 | 5 | 5 | 5 | 5 | 5 | 5 |
| 53 | 2 | 0 | 5 | Dead | | | | | |
| 59 | 2 | 0 | 5 | 5 | 5 | 5 | 5 | Dead | |
| 67 | 2 | 0 | 5 | Dead | | | | | |
| 70 | 2 | 0 | 5 | 5 | Dead | | | | |
| 72 | 2 | 0 | 5 | 5 | 5 | 5 | 5 | 5 | 5 |
| 3 | 3 | 0 | 4 | 5 | 5 | 5 | 5 | Dead | |
| 14 | 3 | 0 | 5 | Dead | | | | | |
| 19 | 3 | 0 | 5 | Dead | | | | | |
| 20 | 3 | 0 | 5 | 5 | 5 | 5 | Dead | | |
| 30 | 3 | 0 | 5 | 5 | 5 | 5 | Dead | | |
| 48 | 3 | 0 | 5 | 5 | 5 | 5 | 5 | 5 | 5 |
| 52 | 3 | 0 | 5 | 5 | 5 | 5 | 5 | 5 | 5 |
| 62 | 3 | 0 | 5 | 5 | Dead | | | | |
| 65 | 3 | 0 | 5 | Dead | | | | | |
| 69 | 3 | 0 | 5 | 5 | Dead | | | | |
| 90 | 3 | 0 | 5 | 5 | 5 | 5 | 5 | 5 | 5 |
| 6 | 4 | 0 | 4 | 3 | 5 | 5 | 5 | 5 | 5 |
| 15 | 4 | 0 | 5 | 5 | 5 | 5 | 5 | 5 | 5 |
| 17 | 4 | 0 | 5 | 5 | 5 | 5 | 5 | 5 | 5 |
| 23 | 4 | 0 | 5 | 5 | 5 | Dead | | | |
| 38 | 4 | 0 | 0 | 5 | | 5 | 5 | 5 | 5 |
| 46 | 4 | 0 | 0 | 5 | 5 | 5 | 5 | 5 | 5 |
| 64 | 4 | 0 | 5 | Dead | | | | | |
| 71 | 4 | 0 | 0 | 3 | 5 | 5 | 5 | 5 | 5 |
| 77 | 4 | 0 | 5 | 5 | 5 | 5 | 5 | 5 | 5 |
| 80 | 4 | 0 | 0 | 5 | 5 | 5 | 5 | 5 | 5 |
| 86 | 4 | 0 | 5 | 4 | 3 | 5 | 5 | 5 | 5 |
| 2 | 5 | 0 | 0 | 4 | 5 | 5 | 5 | 5 | 5 |
| 10 | 5 | 0 | 5 | 5 | 5 | 5 | 5 | 5 | 5 |
| 12 | 5 | 0 | 5 | 5 | 5 | Dead | | | |
| 18 | 5 | 0 | 5 | 5 | Dead | | | | |
| 43 | 5 | 0 | 5 | 5 | 5 | Dead | | | |

TABLE 6-continued

Scores for faecal shedding of *Brachyspira hyodysenteriae* on the days of sampling

| Pig no. | Group | Pre-infection | Days after the first day of experimental infection 7 | 10 | 14 | 17 | 21 | 24 | 28 |
|---|---|---|---|---|---|---|---|---|---|
| 47 | 5 | 0 | 5 | 5 | 5 | 5 | 5 | Dead | |
| 55 | 5 | 0 | 5 | 5 | 5 | Dead | | | |
| 68 | 5 | 0 | 5 | 5 | 5 | 5 | 5 | Dead | |
| 74 | 5 | 0 | 0 | 5 | 3 | 5 | Dead | | |
| 81 | 5 | 0 | 5 | 5 | 5 | 5 | 5 | Dead | |
| 85 | 5 | 0 | 5 | 5 | 5 | 5 | 5 | 5 | 5 |
| 4 | 6 | 0 | 5 | 5 | 5 | Dead | | | |
| 8 | 6 | 0 | 5 | Dead | | | | | |
| 13 | 6 | 0 | 0 | 5 | 5 | 5 | 5 | 5 | 5 |
| 26 | 6 | 0 | 5 | 5 | 5 | 5 | 5 | 5 | 5 |
| 44 | 6 | 0 | 5 | Dead | | | | | |
| 49 | 6 | 0 | 5 | 5 | 5 | 5 | 5 | 5 | 5 |
| 56 | 6 | 0 | 5 | Dead | | | | | |
| 58 | 6 | 0 | 5 | 5 | 5 | 5 | 5 | 5 | 5 |
| 73 | 6 | 0 | 2 | 4 | 5 | 5 | 5 | 5 | 5 |
| 83 | 6 | 0 | 0 | 4 | 5 | 5 | 5 | 5 | 5 |
| 89 | 6 | 0 | 4 | 5 | 5 | 5 | 5 | 5 | 5 |
| 9 | 7 | 0 | 5 | 5 | 5 | 5 | 5 | 5 | 5 |
| 11 | 7 | 0 | 0 | 5 | 5 | 5 | 5 | 5 | 5 |
| 22 | 7 | 0 | 3 | 3 | 4 | 5 | Dead | | |
| 25 | 7 | 0 | 5 | Dead | | | | | |
| 32 | 7 | 0 | 5 | Dead | | | | | |
| 39 | 7 | 0 | 5 | 5 | 5 | Dead | | | |
| 54 | 7 | 0 | 5 | Dead | | | | | |
| 66 | 7 | 0 | 4 | 5 | 5 | 5 | 5 | 5 | 5 |
| 78 | 7 | 0 | 5 | 5 | 5 | 5 | 5 | 5 | 5 |
| 84 | 7 | 0 | 5 | 5 | 5 | Dead | | | |
| 9 | 7 | 0 | 5 | 5 | 5 | 5 | 5 | 5 | 5 |
| 21* | C | 0 | 5 | Dead | | | | | |
| 29 | C | 0 | 5 | Dead | | | | | |
| 35 | C | 0 | 5 | Dead | | | | | |
| 36 | C | 0 | 5 | 5 | 5 | Dead | | | |
| 41 | C | 0 | 5 | 5 | 5 | 5 | Dead | | |
| 50 | C | 0 | 5 | 5 | 5 | Dead | | | |
| 51 | C | 0 | 5 | 5 | Dead | | | | |
| 57 | C | 0 | 5 | 5 | 5 | 5 | 5 | 5 | 5 |
| 63 | C | 0 | 5 | 5 | 5 | Dead | | | |
| 79 | C | 0 | 5 | 5 | 5 | Dead | | | |
| 88 | C | 0 | 5 | Dead | | | | | |

Faecal scores where 0 = no *B. hyodysenteriae*; 0.5 = spirochaetes in the plate stabs; 1 = spirochaetes on the first streak of plate; 2 = spirochaetes on second streak; 3 = spirochaetes on third streak, and so on until 5 = whole surface of the plate covered in spirochaetes. Dead; pig not available for faecal sampling because it was killed. The remaining pigs were killed 5 weeks after the start of the infection process.

*Pig died prior to PM. Culture and observations at necropsy were obtained but no blood/serum was recovered.

TABLE 7

Summary of number of pigs removed for post-mortem at different times following experimental infection.

| Group (n = 11) | Days after the first day of the infection process (day 31 = end of experiment) 8 | 10 | 14 | 15 | 17 | 18 | 21 | 24 | 31 | No. removed before EoE* |
|---|---|---|---|---|---|---|---|---|---|---|
| 1 (OMP6 + OMP7) | 0 | 3 | 0 | 2 | 0 | 2 | 0 | 1 | 3 | 8 |
| 2 (OMP7 + OMP10) | 0 | 1 | 0 | 1 | 0 | 0 | 0 | 0 | 9 | 2 |
| 3 (OMP6 + OMP10) | 1 | 3 | 0 | 2 | 0 | 1 | 0 | 0 | 4 | 7 |
| Negative control | 0 | 4 | 1 | 3 | 1 | 1 | 0 | 0 | 1 | 10 |

*EoE, end of experiment

TABLE 8

Clinical signs, lesions and spirochaete scores in the large intestine shown according to the days following the first day of experimental challenge when the pigs were killed.

| Pig | Group | Day killed[a] | Clinical signs[b] | Lesions[c] Caecum | Colon | Spirochaete score[d] Caecum | Colon | Faeces |
|---|---|---|---|---|---|---|---|---|
| 16 | 1 | 18 | Diarrhoea | N | Mild | 5 | 5 | 5 |
| 24 | 1 | 24 | Dysentery | Moderate | Severe | 5 | 5 | 5 |
| 28 | 1 | 10 | Dysentery | Severe | Severe | 5 | 5 | 5 |
| 31 | 1 | 24 | Dysentery | Mild | Severe | 5 | 5 | 5 |
| 34 | 1 | 24 | Dysentery | Moderate—Severe | Moderate—Severe | 5 | 5 | 5 |
| 37*[#] | 1 | 24 | Dark Diarrhoea | N | Mild | 3 | 5 | 5 |
| 60 | 1 | 31 | Dysentery | Moderate | Moderate—Severe | 5 | 5 | 5 |
| 61 | 1 | 10 | Dysentery | N | Severe | 5 | 5 | 5 |
| 75 | 1 | 31 | Diarrhoea | Mild | Mild—Moderate | 5 | 5 | 5 |
| 76 | 1 | 31 | Diarrhoea | Mild | Mild—Moderate | 5 | 5 | 5 |
| 82 | 1 | 31 | Diarrhoea | N | Mild | 5 | 5 | 5 |
| 1 | 2 | 31 | Diarrhoea | N | Moderate—Severe | 5 | 5 | 5 |
| 7 | 2 | 31 | Diarrhoea | Mild | Mild—Moderate | 5 | 5 | 5 |
| 27 | 2 | 31 | Diarrhoea | N | Mild—Moderate | 5 | 5 | 5 |
| 40 | 2 | 24 | Dysentery | Mild | Moderate—Severe | 5 | 5 | 5 |
| 42 | 2 | 10 | Dysentery | Severe | Severe | 5 | 5 | 5 |
| 45 | 2 | 31 | Dysentery | N | Moderate | 5 | 5 | 5 |
| 53 | 2 | 10 | Dysentery | N | Severe | 5 | 5 | 5 |
| 59 | 2 | 24 | Dysentery | Severe | Severe | 5 | 5 | 5 |
| 67 | 2 | 10 | Dysentery | N | Severe | 5 | 5 | 5 |
| 70 | 2 | 14 | Dysentery | N | Severe | 5 | 5 | 5 |
| 72 | 2 | 31 | Dysentery | N | Moderate—Severe | 5 | 5 | 5 |
| 3 | 3 | 24 | Dysentery | Mild | Severe | 5 | 5 | 5 |
| 14 | 3 | 10 | Dysentery | N | Severe | 5 | 5 | 5 |
| 19 | 3 | 10 | Dysentery | N | Severe | 5 | 5 | 5 |
| 20 | 3 | 18 | Dysentery | N | Moderate—Severe | 5 | 5 | 5 |
| 30 | 3 | 18 | Dysentery | Mild | Moderate | 5 | 5 | 5 |
| 48 | 3 | 31 | Diarrhoea | N | Mild | 5 | 5 | 5 |
| 52 | 3 | 31 | Dysentery | N | Moderate—Severe | 5 | 5 | 5 |
| 62 | 3 | 15 | Dysentery | N | Severe | 5 | 5 | 5 |
| 65 | 3 | 10 | Dysentery | N | Severe | 5 | 5 | 5 |
| 69 | 3 | 15 | Dysentery | N | Severe | 5 | 5 | 5 |
| 90 | 3 | 31 | Dysentery | Mild—Moderate | Moderate—Severe | 5 | 5 | 5 |
| 6 | 4 | 31 | Diarrhoea | N | Mild | 0 | 5 | 5 |
| 15 | 4 | 31 | Diarrhoea | N | N | 1 | 5 | 5 |
| 17 | 4 | 31 | Diarrhoea | N | Mild | 5 | 5 | 5 |
| 23 | 4 | 15 | Dysentery | N | Severe | 5 | 5 | 5 |
| 38 | 4 | 31 | Diarrhoea | N | Mild | 3 | 5 | 5 |
| 46 | 4 | 31 | Dysentery | Mild | Moderate | 5 | 5 | 5 |
| 64 | 4 | 10 | Diarrhoea | Mild | Mild—Moderate | 5 | 5 | 5 |
| 71 | 4 | 31 | Dysentery | Severe | Severe | 5 | 5 | 5 |
| 77 | 4 | 31 | Dysentery | Moderate—Severe | Moderate—Severe | 5 | 5 | 5 |
| 80 | 4 | 31 | Dysentery | N | Severe | 5 | 5 | 5 |
| 86 | 4 | 31 | Diarrhoea | N | Mild | 2 | 5 | 5 |
| 2 | 5 | 31 | Dysentery | N | Severe | 5 | 5 | 5 |
| 10 | 5 | 31 | Dysentery | Moderate | Moderate—Severe | 5 | 5 | 5 |
| 12 | 5 | 15 | Dysentery | Severe | Severe | 5 | 5 | 5 |
| 18 | 5 | 14 | Dysentery | N | Severe | 5 | 5 | 5 |
| 43 | 5 | 15 | Dysentery | N | Moderate—Severe | 5 | 5 | 5 |
| 47 | 5 | 24 | Dysentery | Severe | Severe | 5 | 5 | 5 |
| 55 | 5 | 15 | Dysentery | N | Moderate—Severe | 5 | 5 | 5 |
| 68 | 5 | 24 | Dysentery | Severe | Severe | 5 | 5 | 5 |
| 74 | 5 | 21 | Dysentery | N | Severe | 5 | 5 | 5 |
| 81 | 5 | 24 | Dysentery | Severe | Moderate—Severe | 5 | 5 | 5 |

TABLE 8-continued

Clinical signs, lesions and spirochaete scores in the large intestine shown according to the days following the first day of experimental challenge when the pigs were killed.

| Pig | Group | Day killed[a] | Clinical signs[b] | Lesions[c] Caecum | Lesions[c] Colon | Spirochaete score[d] Caecum | Spirochaete score[d] Colon | Spirochaete score[d] Faeces |
|---|---|---|---|---|---|---|---|---|
| 85 | 5 | 31 | Dysentery | Mild | Moderate—Severe | 5 | 5 | 5 |
| 4 | 6 | 15 | Dysentery | N | Severe | 4 | 5 | 5 |
| 8 | 6 | 10 | Dysentery | N | Moderate—Severe | 4 | 5 | 5 |
| 13 | 6 | 31 | Dysentery | Mild | Moderate | 5 | 5 | 5 |
| 26 | 6 | 31 | Dysentery | Mild | Mild—Moderate | 5 | 5 | 5 |
| 44 | 6 | 10 | Dysentery | N | Severe | 5 | 5 | 5 |
| 49 | 6 | 31 | Dysentery | N | Moderate | 5 | 5 | 5 |
| 56 | 6 | 10 | Dysentery | N | Severe | 5 | 5 | 5 |
| 58 | 6 | 31 | Dysentery | Mild—Moderate | Moderate | 5 | 5 | 5 |
| 73 | 6 | 31 | Diarrhoea | N | Mild | 5 | 5 | 5 |
| 83 | 6 | 31 | Dysentery | Severe | Severe | 5 | 5 | 5 |
| 89 | 6 | 31 | Diarrhoea | N | Mild | 5 | 5 | 5 |
| 9 | 7 | 31 | Diarrhoea | Moderate | Mild | 5 | 5 | 5 |
| 11 | 7 | 31 | Dysentery | N | Severe | 5 | 5 | 5 |
| 22[#] | 7 | 18 | Dark Diarrhoea | N | Mild | 5 | 5 | 3 |
| 25 | 7 | 10 | Dysentery | Mild | Severe | 5 | 5 | 5 |
| 32 | 7 | 8 | Dysentery | N | Severe | 5 | 5 | 5 |
| 39 | 7 | 15 | Dysentery | N | Severe | 5 | 5 | 5 |
| 54 | 7 | 10 | Dysentery | ST | Severe | 5 | 5 | 5 |
| 66 | 7 | 31 | Diarrhoea | N | Mild | 3 | 5 | 5 |
| 78 | 7 | 31 | Dysentery | Mild | Moderate—Severe | 5 | 5 | 5 |
| 84 | 7 | 15 | Dysentery | Mild | Moderate—Severe | 5 | 5 | 5 |
| 87 | 7 | 10 | Dysentery | N | Severe | 5 | 5 | 5 |
| 21 | 8 | 10 | Dysentery | Mild—Moderate | Severe | 5 | 5 | 5 |
| 29 | 8 | 10 | Dysentery | N | Severe | 5 | 5 | 5 |
| 35 | 8 | 10 | Dysentery | N | Severe | 5 | 5 | 5 |
| 36 | 8 | 15 | Dysentery | Mild | Moderate—Severe | 5 | 5 | 5 |
| 41 | 8 | 18 | Dysentery | Moderate—Severe | Severe | 5 | 5 | 5 |
| 50 | 8 | 15 | Dysentery | N | Severe | 5 | 5 | 5 |
| 51 | 8 | 14 | Dysentery | Severe | Severe | 5 | 5 | 5 |
| 57 | 8 | 31 | Dysentery | Mild | Moderate—Severe | 5 | 5 | 5 |
| 63 | 8 | 17 | Dysentery | Severe | Severe | 5 | 5 | 5 |
| 79 | 8 | 15 | Dysentery | N | Severe | 5 | 5 | 5 |
| 88 | 8 | 10 | Dysentery | N | Severe | 5 | 5 | 5 |

[a]Days following the first day of spirochaete challenge

[b]Clinical signs: "dysentery" necessitating killing of the pig; "diarrhoea" was prolonged diarrhoea that together with severe loss of bodily condition necessitated killing the pig before the end of the experiment; "normal" represented no clinical signs at the end of the experimental period.

[c]Gross pathology: N, normal; Mild, mild or patchy inflammation; Mild-Moderate, mild inflammation with mild localised colitis; Moderate, moderate localised colitis; Moderate-Severe, moderate colitis with localised mucohaemorhagic lesions; Severe, severe mucohaemorhagic lesions.

[d]Culture scores where 0 = no *B. hyodysenteriae*; 1 = spirochaetes on first streak of the plate; 2 = spirochaetes on the second streak; 3 = spirochaetes on the third streak, and so on until 5 = whole surface of the plate covered in spirochaetes.

*Pig died prior to PM. Culture and observations at necropsy were obtained but no blood/serum was recovered.

[#]Pig removed due to presence of dark faeces indicative of peptic ulcer.

TABLE 9

Summary of occurrence (and percentage) of pigs with clinical signs and gross lesions in the large intestine at post-mortem for the four groups of pigs.

| Group (n = 11) | Clinical signs Diarrhoea | Clinical signs Dysentery | Total number with lesions | Lesions in the colon: Number with mild lesions | Number with mild/mod lesions | Number with moderate lesions | Number with mod/severe lesions | Number with severe lesions |
|---|---|---|---|---|---|---|---|---|
| 1 | 1 (9) | 10 (91) | 11 | 1 (9) | 0 | 1 (9) | 3 (27) | 6 (55) |
| 2 | 6 (55) | 5 (45) | 10 | 4 (36) | 1 (9) | 1 (9) | 1 (9) | 3 (27) |
| 3 | 3 (27) | 8 (73) | 11 | 3 (27) | 0 | 0 | 2 (18) | 6 (55) |
| 4 | 0 | 11 (100) | 11 | 0 | 0 | 0 | 2 (18) | 9 (82) |

TABLE 10

Summary (and percentage) of pigs with gross lesions in the large intestine at post-mortem for the four groups of pigs

| Group (n = 11) | Post-mortem observations Normal | Mild | Mild/ Mod | Moderate | Mod/ Severe | Severe |
|---|---|---|---|---|---|---|
| 1 | 0 | 1 (9) | 0 | 1 (9) | 3 (27) | 6 (55) |
| 2 | 1 (9) | 4 (36) | 1 (9) | 1 (9) | 1 (9) | 3 (27) |
| 3 | 0 | 3 (27) | 0 | 0 | 2 (18) | 6 (55) |
| 4 | 0 | 0 | 0 | 0 | 2 (18) | 9 (82) |

TABLE 11

Summary (and percentage) of pigs with normal to mild/moderate or moderate to severe gross lesions in the large intestine at post-mortem for the four groups of pigs

| Group (n = 11) | Vaccine components | Post-mortem observations Normal/Mild/ Mild Mod | Mod/Mod Sever/Severe |
|---|---|---|---|
| 1 | OMP6, OMP7 | 1 (9) | 10 (91) |
| 2 | OMP7, OMP10 | 6 (55) | 5 (45) |
| 3 | OMP6, OMP10 | 3 (27) | 8 (73) |
| 4 | Negative control | 0 | 11 (100) |

The invention claimed is:

1. An isolated cell comprising a vector comprising a polynucleotide encoding at least one polypeptide selected from the group consisting of:

a. the polypeptide comprising or consisting of SEQ ID NO: 1;

b. a polypeptide comprising or consisting of SEQ ID NO: 3;

c. a polypeptide comprising or consisting of SEQ ID NO: 5, and d. a combination of the polypeptides of (a) and (b), (a) and (c), or (a), (b), and (c).

2. A vector for the expression of at least one *Brachyspira* hyodysenteriae recombinant protein encoded in a polynucleotide sequence selected from the group consisting of:

a. a polynucleotide comprising SEQ ID NO: 2;

b. a polynucleotide comprising SEQ ID NO: 4;

c. a polynucleotide comprising SEQ ID NO: 6; and d. a combination of polynucleotides from (a) and (b), or (a) and (c), or (a), (b) and (c).

3. A vaccine composition for the treatment or prevention of clinical signs caused by *Brachyspira hyodysenteriae* or a disease caused by *Brachyspira hyodysenteriae* comprising the vector of claim 2.

4. A method of treating or preventing a disease caused by *Brachyspira* hyodysenteriae in an animal in need of said treatment comprising administering to said animal a therapeutically effective dose of the vaccine composition of claim 3.

5. An isolated cell expressing at least one *Brachyspira* hyodysenteriae recombinant protein, wherein said cell contains at least one vector comprising a polynucleotide sequence selected from the group consisting of:

a. a polynucleotide comprising SEQ ID NO:2;

b. a polynucleotide comprising SEQ ID NO: 4;

c. a polynucleotide comprising SEQ ID NO: 6; and d. a combination of polynucleotides of (a) and (b), (a) and (c), or (a), (b), and (c).

6. An immunogenic composition comprising the vector of claim 2.

7. The immunogenic composition of claim 6, wherein said vector is a baculovirus.

8. The vector according to claim 2, wherein the vector is a plasmid.

9. A diagnostic kit for the detection of *B. hyodysenteriae* infection in an animal comprising an oligonucleotide at least eight nucleotides in length, the oligonucleotide being complementary to a portion of SEQ ID NO:2, and/or sequences that are at least 90% identical to SEQ ID NO:2.

10. The diagnostic kit of claim 9, further comprising:

a. an oligonucleotide at least eight nucleotides in length, the oligonucleotide being complementary to a portion of SEQ ID NO:4, and/or sequences that are at least 90% identical to SEQ ID NO:4; and b. an oligonucleotide at least eight nucleotides in length, the oligonucleotide being complementary to a portion of SEQ ID NO: 6, and/or sequences that are at least 90% identical to SEQ ID NO:6.

11. A diagnostic kit for the detection of *B. hyodysenteriae* infection in an animal containing a polynucleotide having at least 90% sequence identity to SEQ ID NO:2.

12. The diagnostic kit of claim 11, further containing:

a. a polynucleotide having at least 90% sequence identity to SEQ ID NO:4 and/or b. a polynucleotide having at least 90% sequence identity to SEQ ID NO:6.

13. A diagnostic kit for the detection of *B. hyodysenteriae* in an animal comprising a recombinant protein consisting of SEQ ID NO:1 coupled with a detectable label selected from the group consisting of a radioactive element, an enzyme, and a fluorescent chemical.

14. The diagnostic kit of claim 13, further containing:

a. a recombinant protein having a sequence consisting of SEQ ID NO: 3; and/or b. a recombinant protein having a sequence consisting of sequence of SEQ ID NO: 5.

15. A method for detecting *B. hyodysenteriae* in a biological sample comprising the steps of:

a. obtaining a biological sample containing at least one nucleic acid from an animal;

b. providing a forward and a reverse-oligonucleotide primer pair wherein the forward and reverse oligonucleotide primers are at least eight nucleotides in length, the oligonucleotide being complementary to a portion of SEQ ID NOs:2, or at least 95% identical to a portion of SEQ ID NO:2;

c. contacting the oligonucleotide primer pair with the biological sample under conditions that permit polymerase chain reaction (PCR) detection of the nucleic acid-containing biological sample having at least 95% sequence identity to SEQ ID NO:2;

d. generating a PCR product; and e. detecting the PCR product wherein the presence of the PCR product indicates *B. hyodysenteriae* infection and/or immunization with *B. hyodysenteriae* in the biological sample.

16. A method for detecting *B. hyodysenteriae* infection and/or immunization with *B. hyodysenteriae* in a biological sample comprising the steps of:

a. obtaining a biological sample containing at least one circulating antibodies to *B. hyodysenteriae* from an animal;

b. providing a *B. hyodysenteriae* polypeptide, or a fragment thereof, having at least 95% identity SEQ ID NO:1;

c. contacting the *B. hyodysenteriae* polypeptide, or fragment thereof with the biological sample under conditions that permit binding of the *B. hyodysenteriae* polypeptide with the antibodies of the biological sample; and d. detecting the presences of antibody-*B. hyodysenteriae* polypeptide complexes, wherein detecting the presence of antibody-*B. hyodysenteriae* polypeptide complexes indicates *B. hyodysenteriae* infection and/or immunization in the biological sample.

17. The vector of claim 2, wherein the at least one *Brachyspira hyodysenteriae* recombinant protein consists of SEQ ID NO:1 encoded in the polynucleotide sequence comprising SEQ ID NO: 2.

18. The vector of claim 2, wherein said vector is a baculovirus.

19. A method for the treatment or prevention of clinical signs caused by *Brachyspira hyodysenteriae* or a disease caused by *Brachyspira hyodysenteriae* comprising administering a therapeutically effective immunogenic composition comprising the vector of claim 2, to an animal in need thereof.

20. A method of generating an immune response to *Brachyspira hyodysenteriae* in an animal comprising administering to said animal the vector of claim 2.

21. A recombinantly expressed polypeptide expressed by the vector of claim 2, admixed with at least one of the group selected from a pharmaceutically acceptable diluent, excipients, preservatives, solubilizers, emulsifiers, adjuvants and/or carriers.

* * * * *